United States Patent
Homan et al.

(10) Patent No.: US 7,881,668 B2
(45) Date of Patent: Feb. 1, 2011

(54) RECEIVING APPARATUS FOR SWALLOW-TYPE CAPSULE ENDOSCOPE

(75) Inventors: Masatoshi Homan, Hino (JP); Akira Matsui, Hino (JP); Toshiaki Shigemori, Hachioji (JP); Takeshi Mori, Machida (JP); Noriyuki Fujimori, Suwa (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 371 days.

(21) Appl. No.: 12/052,941

(22) Filed: Mar. 21, 2008

(65) Prior Publication Data

US 2008/0227394 A1    Sep. 18, 2008

Related U.S. Application Data

(63) Continuation of application No. PCT/JP2006/318772, filed on Sep. 21, 2006.

(30) Foreign Application Priority Data

| Sep. 22, 2005 | (JP) | 2005-275666 |
| Sep. 29, 2005 | (JP) | 2005-284625 |
| Oct. 26, 2005 | (JP) | 2005-311664 |

(51) Int. Cl.
*H04B 7/00* (2006.01)
(52) U.S. Cl. ............ 455/41.3; 455/67.11; 600/424
(58) Field of Classification Search .......... 455/41.1, 455/41.2, 41.3, 63.4, 66.1, 67.11, 133, 134, 455/161.3, 327; 370/342, 441; 600/424, 600/419, 407, 410, 411, 425; 606/2, 20, 606/27, 32; 324/307, 308, 309
See application file for complete search history.

(56) References Cited

U.S. PATENT DOCUMENTS

| 4,633,304 | A | 12/1986 | Nagasaki |
| 6,522,642 | B1 * | 2/2003 | Scott .................. 370/342 |
| 6,612,981 | B2 | 9/2003 | Onishi et al. |
| 6,840,901 | B2 | 1/2005 | Onishi et al. |
| 6,853,310 | B2 | 2/2005 | Brinsfield |

(Continued)

FOREIGN PATENT DOCUMENTS

| FR | 2833739 A1 | 6/2003 |
| JP | 2001-231186 | 8/2001 |
| JP | 2001-353124 | 12/2001 |

(Continued)

OTHER PUBLICATIONS

Supplementary European Search Report dated Jun. 22, 2010.

*Primary Examiner*—Lana N Le
*Assistant Examiner*—Ping Y Hsieh
(74) *Attorney, Agent, or Firm*—Scully, Scott, Murphy & Presser, P.C.

(57) ABSTRACT

A receiving apparatus is for receiving radio signals including image information transmitted by a mobile transmitting device through a plurality of receiving antennas. The receiving apparatus includes a plurality of frequency converters for outputting modulated signals obtained by converting respective radio signal received through the plurality of receiving antennas by different modulation frequencies; a superposing unit for superposing each of the modulated signals generated by the plurality of frequency converters on a frequency axis; a cable with a single coaxial cable where each of the modulated signals superposed by the superposing unit is transmitted; and a receiving unit for demodulating each modulated signal input through the cable to receive and output the image information.

5 Claims, 25 Drawing Sheets

U.S. PATENT DOCUMENTS

| | | |
|---|---|---|
| 6,902,529 B2 | 6/2005 | Onishi et al. |
| 6,904,308 B2 | 6/2005 | Frisch et al. |
| 2002/0111149 A1* | 8/2002 | Shoki .................. 455/277.1 |
| 2002/0173718 A1* | 11/2002 | Frisch et al. ............... 600/424 |
| 2003/0062476 A1 | 4/2003 | Wang |
| 2004/0104999 A1 | 6/2004 | Okada |

FOREIGN PATENT DOCUMENTS

| | | |
|---|---|---|
| JP | 2003-19111 | 1/2003 |
| JP | 2003-526268 | 9/2003 |
| JP | 2004-167163 | 6/2004 |
| JP | 2006-239170 | 9/2006 |
| WO | WO 00/30540 A1 | 6/2000 |

* cited by examiner

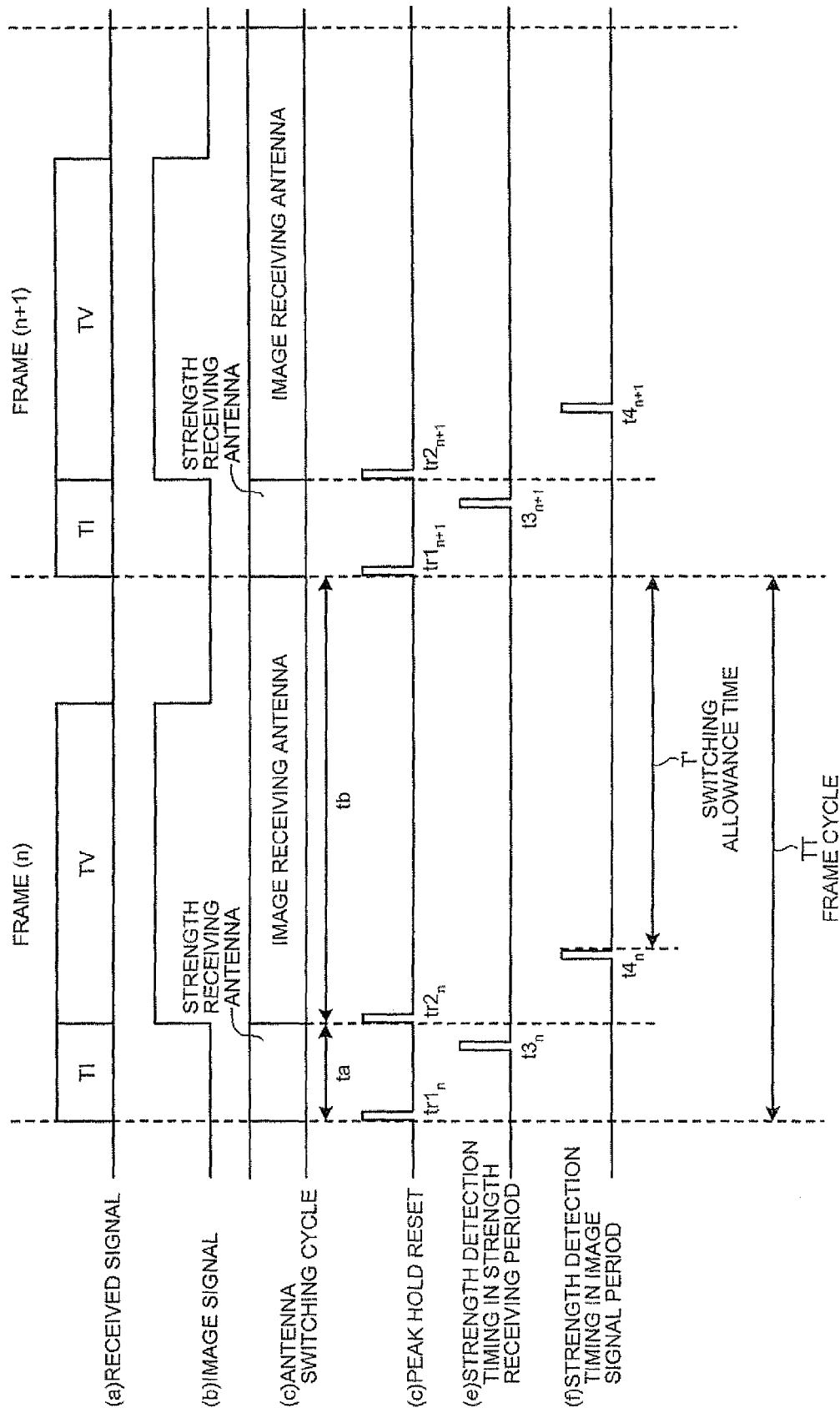

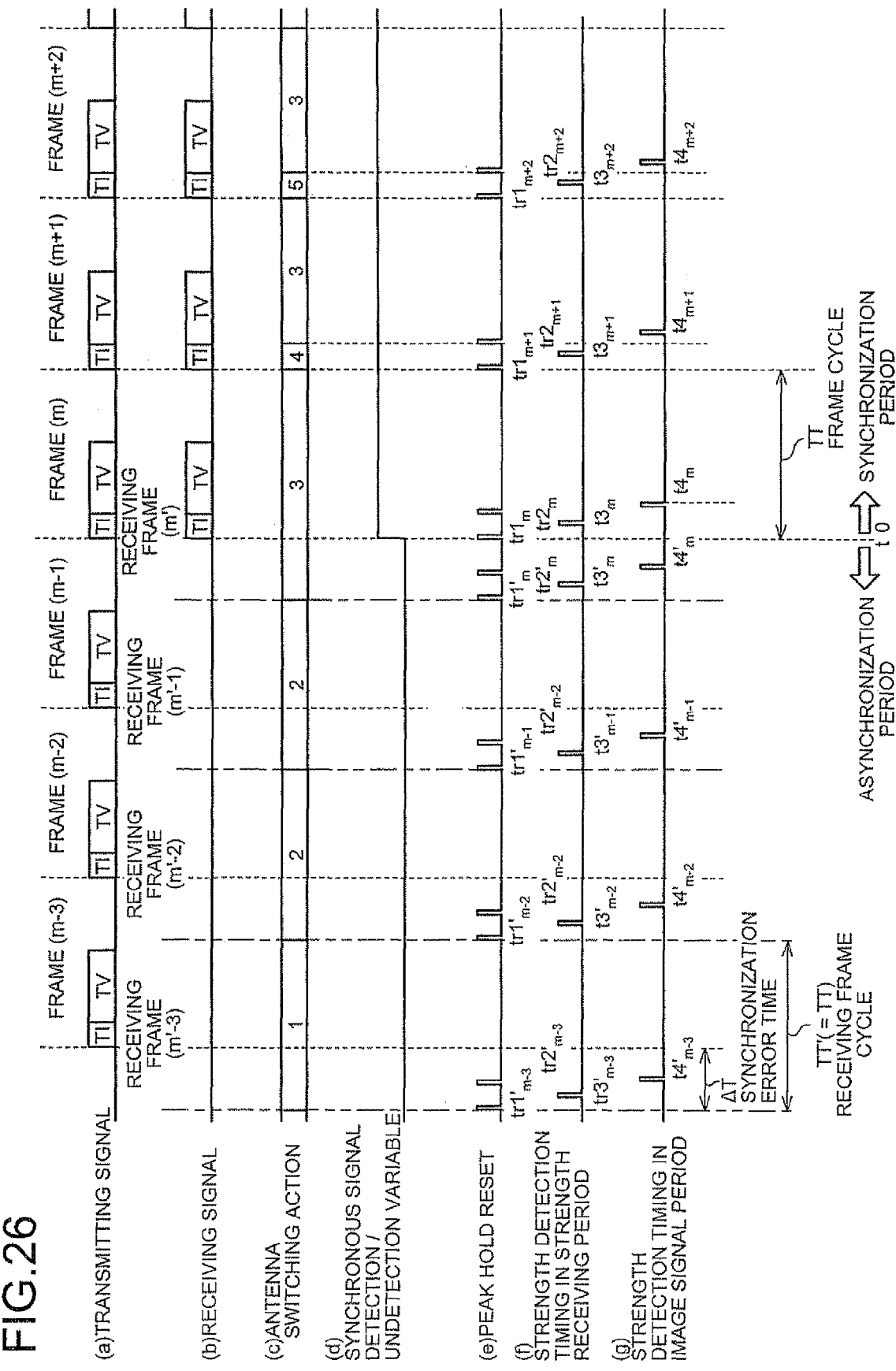

RECEIVING APPARATUS FOR SWALLOW-TYPE CAPSULE ENDOSCOPE

CROSS-REFERENCE TO RELATED APPLICATIONS

This application is a continuation of PCT international application Ser. No. PCT/JP2006/318772 filed Sep. 21, 2006 which designates the United States, incorporated herein by reference, and which claims the benefit of priority from Japanese Patent Applications No. 2005-275666, filed Sep. 22, 2005; No. 2005-284625, filed Sep. 29, 2005; and No. 2005-311664, filed Oct. 26, 2005, incorporated herein by reference.

BACKGROUND OF THE INVENTION

1. Field of the Invention

The present invention relates to a receiving apparatus for receiving radio signal including image information which a movable transmitting unit transmits through a plurality of receiving antennas.

2. Description of the Related Art

In recent years, in the field of the endoscope, a swallow-type capsule endoscope has appeared. This capsule endoscope is provided with image pickup function and radio communication function. The capsule endoscope has a function of being moved following the peristaltic motion inside of the body cavity, for example, the inside of the organs such as the stomach, small intestine after it is swallowed through the mouth of a patient for observation (examination) until it is naturally excreted from the body so as to take the images sequentially.

Image information taken by the capsule endoscope inside of the body while it is moved inside of the body cavity is transmitted to outside in succession by radio signals and stored in a memory provided in a receiving apparatus outside. By carrying the receiving apparatus equipped with the receiving function and memory function, the patient can move freely after he or she swallows the capsule endoscope until the capsule type is excreted. After that, a medical doctor or nurse can display images of the organ based on the image data stored in the memory on a display device for diagnosis.

Generally in the receiving apparatus, a plurality of receiving antennas for receiving a radio signal transmitted from the capsule endoscope are disposed dispersedly outside of the body and a single receiving antenna having fewer reception errors in the radio signal is selected so as to receive the radio signal. In the meantime, a receiving apparatus which detects the position of a capsule endoscope inside the body which transmits out the image signal according to the strength of signal received by each receiving antenna by switching receiving of the plurality of receiving antennas disposed outside of the body has been disclosed (see Japanese Patent Application Laid-Open No. 2003-19111).

SUMMARY OF THE INVENTION

A receiving apparatus of an aspect of the present invention is for receiving radio signals including image information transmitted by a mobile transmitting device through a plurality of receiving antennas, and includes a plurality of frequency converters for outputting modulated signals obtained by converting respective radio signal received through the plurality of receiving antennas by different modulation frequencies; a superposing unit for superposing each of the modulated signals generated by the plurality of frequency converters on a frequency axis; a cable with a single coaxial cable where each of the modulated signals superposed by the superposing unit is transmitted; and a receiving unit for demodulating each modulated signal input through the cable to receive and output the image information.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 25 is a time chart showing the received electric field strength measuring processing of each frame by the receiving apparatus shown in FIG. 24; and FIG. 26 is a time chart showing the synchronous restoration antenna switching processing by the receiving apparatus shown in FIG. 24.

DETAILED DESCRIPTION OF THE PREFERRED EMBODIMENTS

Hereinafter the preferred embodiments of the receiving apparatus of the present invention will be described in detail with reference to the accompanying drawings.

Figure 1:
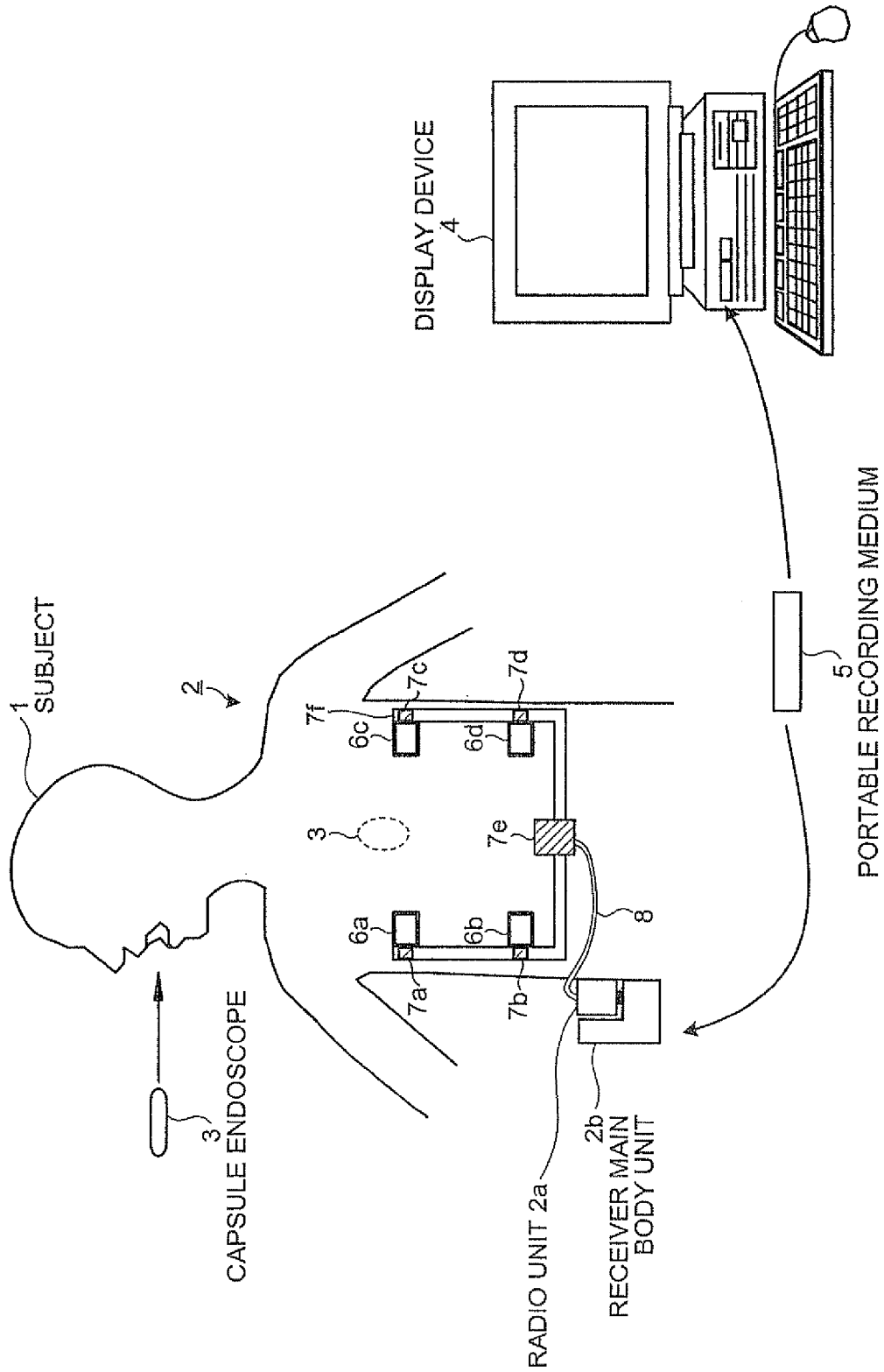
FIG. 1 is a diagram showing the schematic configuration of a capsule endoscope system including a receiving apparatus according to a first embodiment of the present invention.

FIG. 1 is a diagram showing the schematic configuration of a capsule endoscope examination system including a receiving apparatus according to a first embodiment of the present invention. Referring to FIG. 1, when the capsule endoscope 3 is introduced into a subject 1, the capsule endoscope 3 is moved inside of the organ following the peristaltic motion so as to take pictures of the inside of the organ and transmits taken image information to the outside of the body as transmitting signals. A receiving apparatus 2 receives this transmitting signal through a plurality of antennas 6a to 6d and acquires a series of images taken by the capsule endoscope 3 in a period until the capsule endoscope 3 is discharged out of the subject 1 or in a desired period until it is discharged out of the subject 1 and stores in a portable recording medium 5. This portable recording medium 5 is mounted detachably to the receiving apparatus 2 or a display device 4 and image information stored in the portable recording medium 5 is displayed when it is mounted on the display device 5 and analyzed.

The receiving apparatus 2 includes a plurality of receiving antennas 6a to 6d, frequency converting units 7a to 7d which are connected to the receiving antennas 6a to 6d so as to convert the received signals to different frequencies, a superposing unit 7e for outputting respective modulated signals output from the frequency converting units 7a to 7d such that they are superposed on the frequency axis, a flexible substrate 7f in which wirings for connecting the frequency converting units 7a to 7d to an adder unit 7e is disposed, a radio unit 2a for demodulating the modulated signal input from the superposing unit 7e so as to generate a base band signal, a single coaxial cable 8 for connecting the superposing unit 7e to the radio unit 2a and a receiver main body unit 2b which is connected to the radio unit 2a so as to generate and output image information based on the base band signal input from the radio unit 2a.

Figure 2:
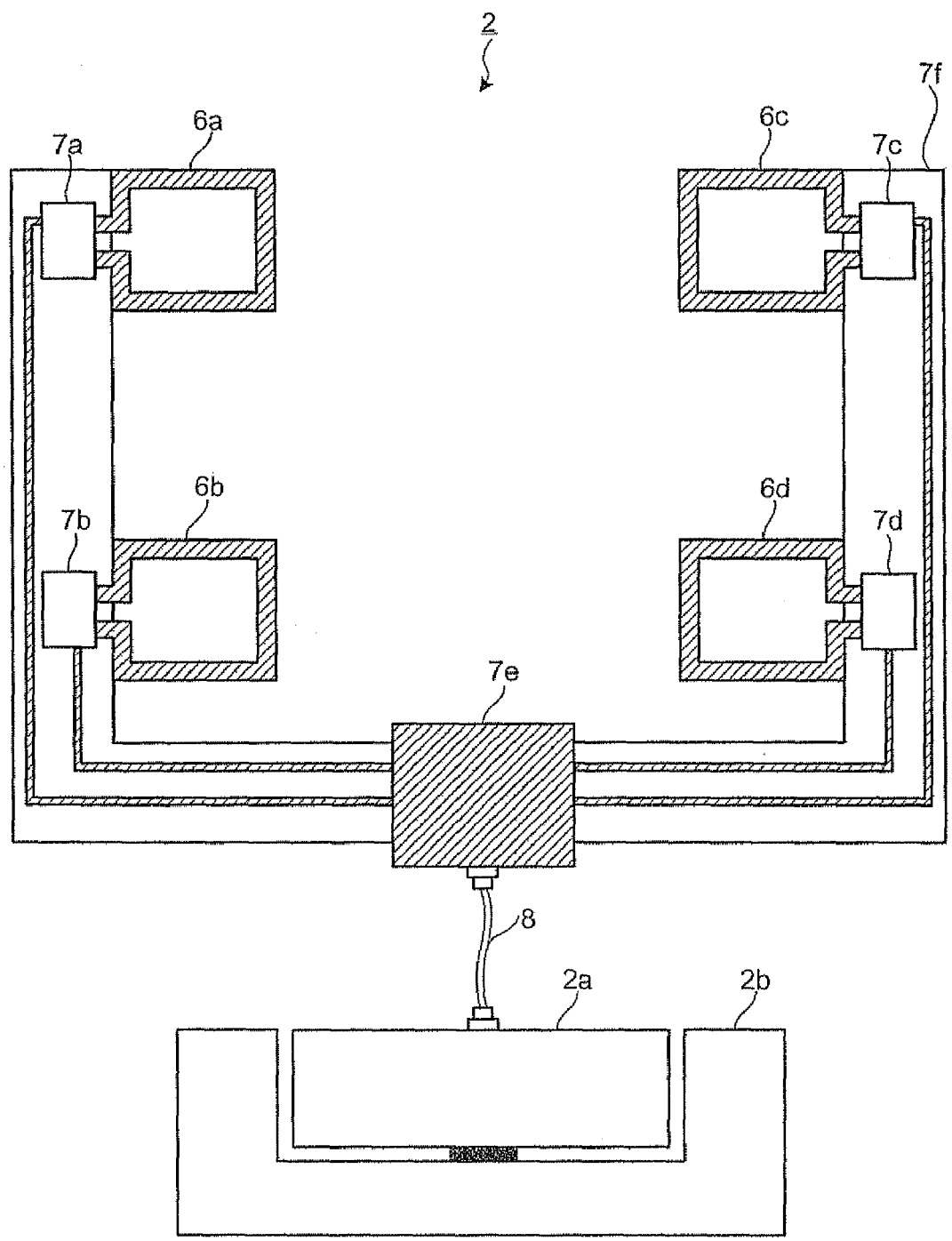
FIG. 2 is a diagram showing an exterior appearance of the configuration of the receiving apparatus shown in FIG. 1.

FIG. 2 is a diagram showing an external appearance of the schematic configuration of this receiving apparatus 2. As shown in FIG. 2, the receiving antennas 6a to 6d are formed of printed wiring and the frequency converting units 7a to 7d are formed of a planar circuit and wires for connecting the frequency converting units 7a to 7d to the radio unit 2a are disposed on the flexible substrate 7f.

Figure 3:
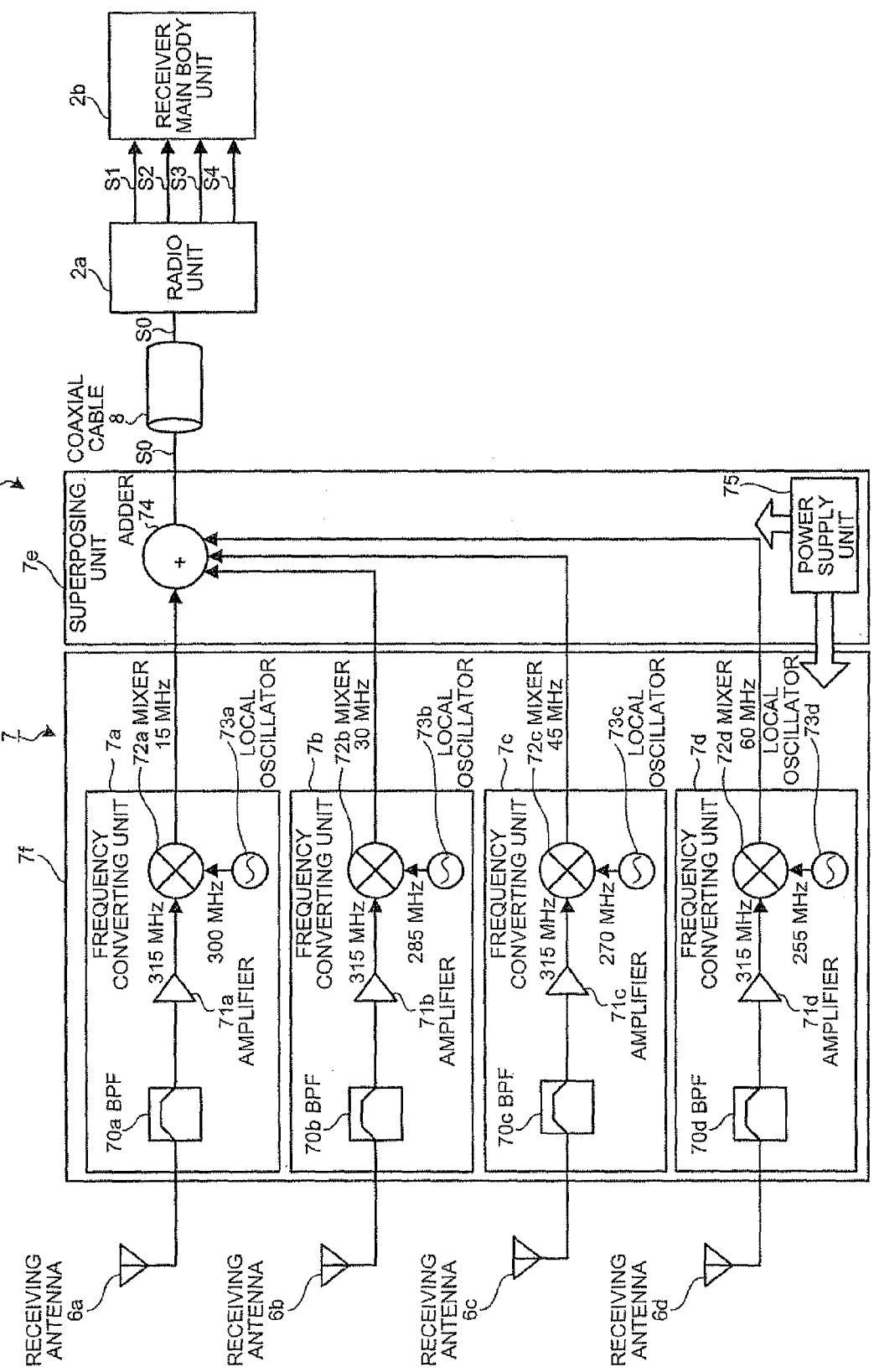
FIG. 3 is a block diagram showing the detailed configuration of a modulation unit and a superposing unit of the receiving apparatus shown in FIG. 1.
Figure 4:
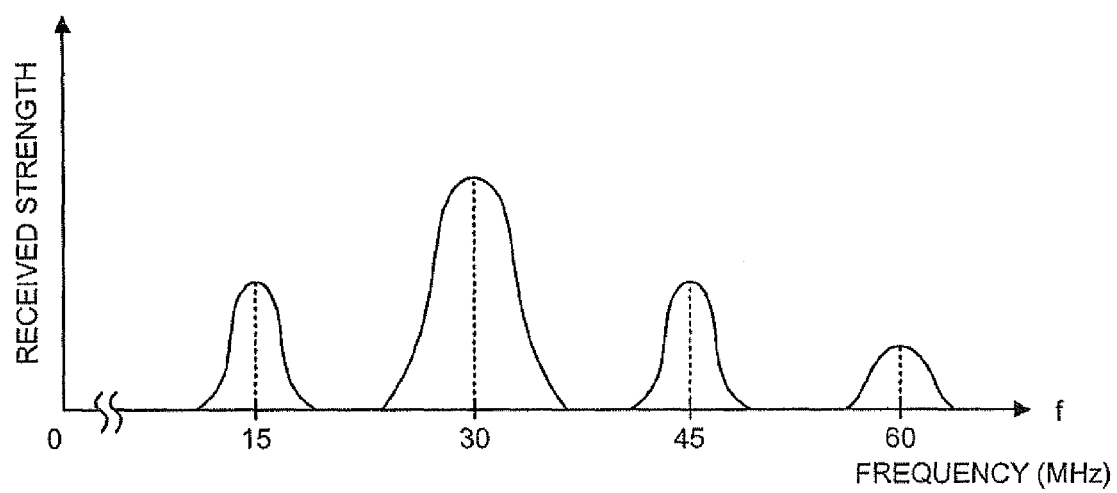
FIG. 4 is a diagram showing an example of the modulated signal superposed on a frequency axis.

FIG. 3 is a block diagram showing the configuration of the receiving apparatus 2 including the detailed configuration of the frequency converting units 7a to 7d and the superposing unit 7e. As shown in FIG. 3, the frequency converting units 7a to 7d include band pass filters (BPF) 70a to 70d which allow only a transmitting signal band of the signals received by the receiving antennas 6a to 6d, amplifiers 71a to 71d which amplify and output the signals passing the BPF 70a to 70d, local oscillators 73a to 73d which oscillate different frequency signals and mixers 72a to 72d which mix signals output from the amplifiers 71a to 71d with frequency signals output from the local oscillators 73a to 73d. The superposing unit 7e has an adder 74, and the adder 74 adds signals output from the mixers 72a to 72d, superposes them on the frequency axis as shown in FIG. 4 and outputs to the radio unit 2a side through the coaxial cable 8. The superposing unit 7e has a power supply unit 75 constituted of a secondary battery or the like and the power supply unit 75 supplies electricity to the adder 74 inside the superposing unit 7e and the respective frequency converting units 7a to 7d on the flexible substrate 7f.

The transmitting signals in 315 MHz band received by the receiving antennas 6a to 6d are input to the mixers 72a to 72d through the BPFs 70a to 70d and the amplifiers 71a to 71d, and the respective mixers 72a to 72d mix the frequency signals of 300 MHz, 285 MHz, 270 MHz and 255 MHz output from the local oscillators 73a to 73d with signals from the mixers 72a to 72d and output as frequency conversion signals of 15 MHz, 30 MHz, 45 MHz and 60 MHz to the adder 74. The adder 74 adds respective modulated signals and outputs a superposing signal S0 superposed on the frequency axis to the radio unit 2a through the coaxial cable 8 as shown in FIG. 4.

Figure 5:
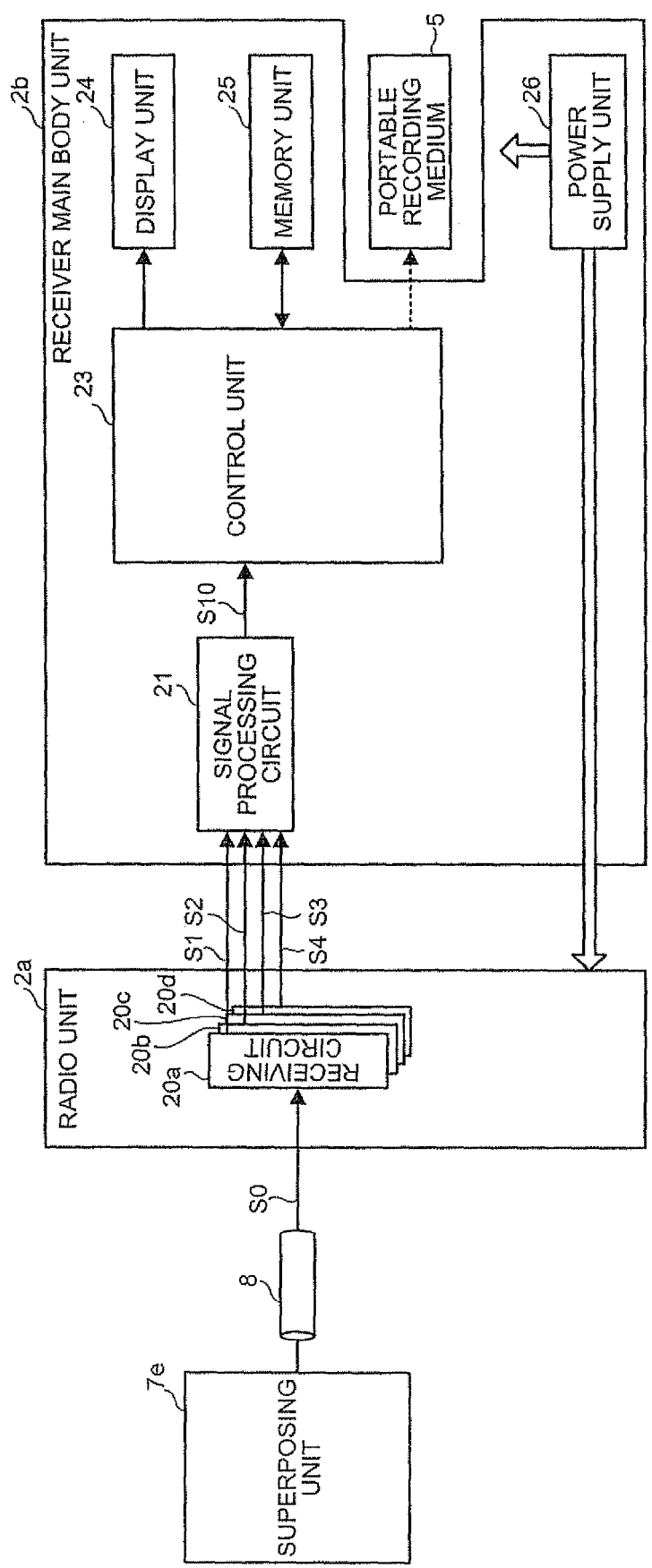
FIG. 5 is a block diagram showing the detailed configuration of a radio unit and receiver main body unit of the receiving apparatus shown in FIG. 1.

FIG. 5 is a block diagram showing the detailed configuration of the radio unit 2a and the receiver main body unit 2b. As shown in FIG. 5, the radio unit 2a has receiving circuits 20a to 20d corresponding to the number of the input modulated signals and the receiving circuits 20a to 20d demodulate modulated signals (15 MHz, 30 MHz, 45 MHz, 60 MHz) of the superposing signal S0 and output base band signals S1 to S4 to the receiver main body unit 2b. The receiver main unit 2b includes a signal processing circuit 21 which processes the base band signals S1 to S4 so as to generate likelihood image information S10, a display unit 24 which displays and outputs various statuses, a memory unit 25 for holding various kinds of programs and data and a power supply unit 26 for supplying electricity to the receiver main body unit 2b and the radio unit 2a. In the meantime, the portable recording medium 5 records a series of image information output form the signal processing circuit 21.

In other words, the signal processing circuit 21 simultaneously demodulates the base band signals S1 to S4 simultaneously input from the receiving circuits 20a to 20d and generates single image information S10 which is a demodulation result having few errors and this generated image information S10 is recorded in the portable recording medium 5. In the meantime, the signal processing circuit 21 may generate and output single image information S10 using four base band signals S1 to S4 without selecting the single image information S10 having few errors.

According to the first embodiment, the frequency converting units 7a to 7d for generating different modulated signals are provided and the respective modulated signals are superposed by the superposing unit 7e and then, this superposing signal S0 is transmitted to the radio unit 2a side through the single coaxial cable 8. Consequently, the number of wirings between the plurality of antennas 6a to 6d and the radio unit 2a can be reduced thereby preventing occurrence of trouble such as breaking of the wires due to entangling of the wires. Further, the respective modulated signals are demodulated at the same time so as to generate single likelihood image information S10 and consequently, even an image taken in the esophagus in which the capsule endoscope is moved at a high speed can be prevented from being skipped.

FIG. 4 is a schematic diagram showing the signal strength of a frequency of the image signal S0. As shown in FIG. 4, the image signal S0 has a peak at every 15, 30, 45, 60 MHz in frequency and the signal strength of the frequency 30 MHz is at the maximum. In other words, the signal strength of an image signal received through the receiving antenna 6b is at the maximum level.

Although the four receiving antennas 6a to 6d, the four frequency converting units 7a to 7d and the four receiving circuits 20a to 20d of this the first embodiment are provided, the present invention is not limited to this number. Further, although according to the first embodiment, the radio unit 2a and the receiver main body unit 2b are separated, the present invention is not limited to this but the radio unit 2a and the receiver main body unit 2b may be integrated. Further, although the receiving circuits 20a to 20d of the radio unit 2a are provided in the radio unit 2a, it is permissible to provide part of the receiving circuits 20a to 20d on the radio unit 2a side while the remaining structure is provided on the receiver main body unit 2b side.

Next, a second embodiment of the present invention will be described. Although according to the first embodiment, the signal processing circuit 21 generates image information based on the base band signals S1 to S4 output from the receiving circuits 20a to 20d, in the second embodiment, any one of the receiving circuits 20a to 20d is selected and the signal processing circuit processes a base band signal output from the selected one of the receiving circuits 20a to 20d so as to generate the image signal S10.

Figure 6:
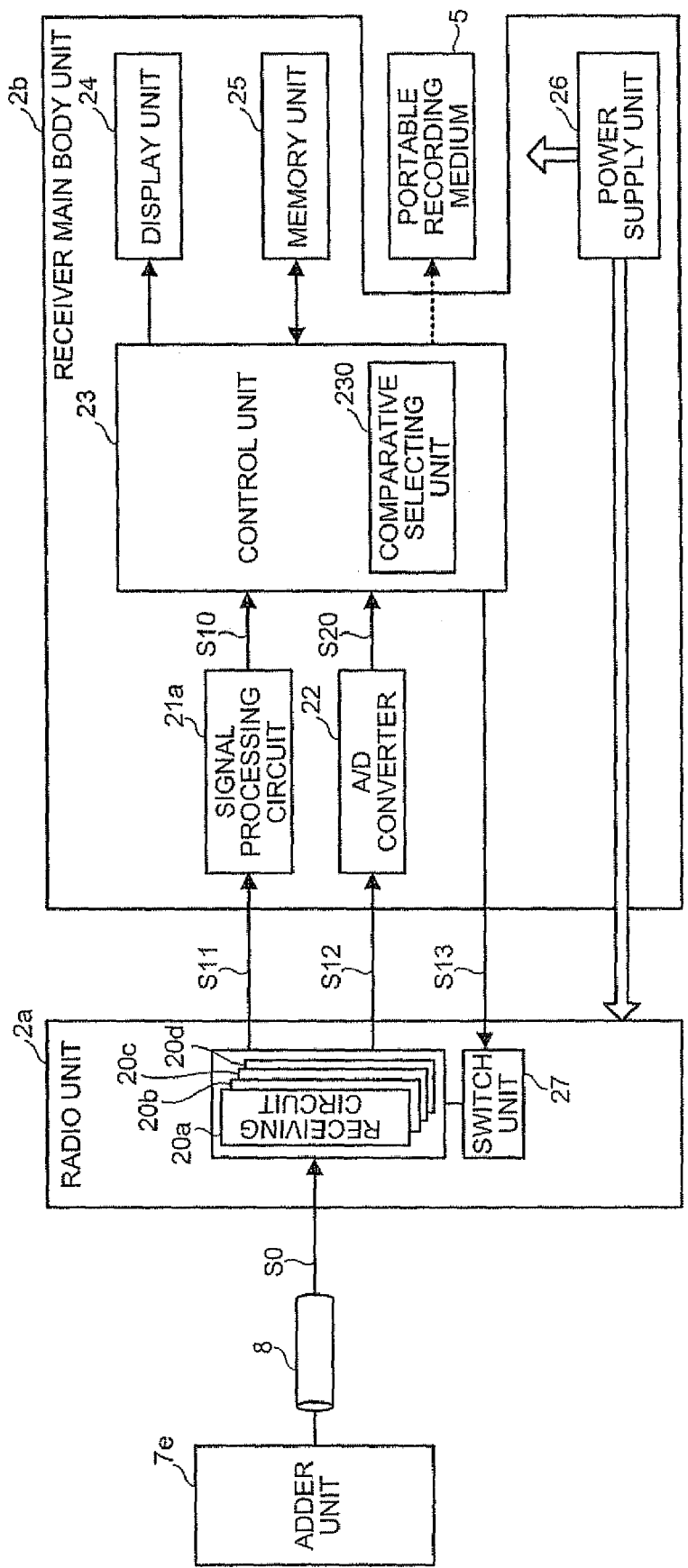
FIG. 6 is a block diagram showing the detailed configuration of the radio unit and receiver main body unit according to a second embodiment of the present invention.

FIG. 6 is a block diagram showing the detailed configuration of the radio unit 2a and the receiver main body unit 2b according to the second embodiment of the present invention. As shown in FIG. 6, the radio unit 2a is provided with a switch unit 27 as well as the structure of the radio unit 2a shown in FIG. 5 and this switch unit 27 outputs the base band signal S11 from one of the receiving circuits 20a to 20d instructed by a switching signal S13 input from the receiver main body unit 2b to the receiver main body unit 2b side. In the meantime, the receiving circuits 20a to 20d output a reception strength signal S12 indicating the reception strength of each modulated signal to the receiver main body unit 2b side.

The signal processing circuit 21a generates image information S10 based on the base band signal S11 input from the radio unit 2a and the control unit 23 records this image information S10 in the portable recording medium 5. On the other hand, the A/D converter 22 converts the received strength signal S12 input from the respective receiving circuits 20a to 20d to digital signal and outputs to the control unit 23. The control unit 23 has a comparison selecting unit 230 and this comparison selecting unit 230 outputs switching signal S13 for selecting one of the receiving circuits 20a to 20d which outputs a signal of the highest received strength to the switch unit 27 on the radio unit 2a side based on a digital signal S20 indicating the received strength input from the A/D converter 22. For example, if the received strength of each modulated signal indicates a value as shown in FIG. 4, the switching signal S13 which selects the receiving circuit 20b for generating a modulated signal of 30 MHz for switching is output to the switch unit 27.

According to this the second embodiment, a plurality of frequency converting units 7a to 7d for generating different modulated signals are provided and the respective modulated signals are superposed by the superposing unit 7e and this superposing signal S0 is transmitted to the radio unit 2a side through the single coaxial cable 8. Consequently, the number of wires between the plurality of antennas 6a to 6d and the radio unit 2a can be reduced thereby preventing occurrence of trouble such as breaking of the wire due to entangling of the wires. Further, the receiving circuits 20a to 20d are selected and switched and the signal processing circuit 21a generates image information S10 based on single base band signal input from the selected receiving circuits 20a to 20d, thereby the structure of the receiving apparatus 2 being entirely simplified. Further, because each of the receiving circuits 20a to 20d generates the base band signal by performing synchronous processing on each modulated signal independently, quick switching is enabled thereby preventing the image information from being skipped.

Figure 7:
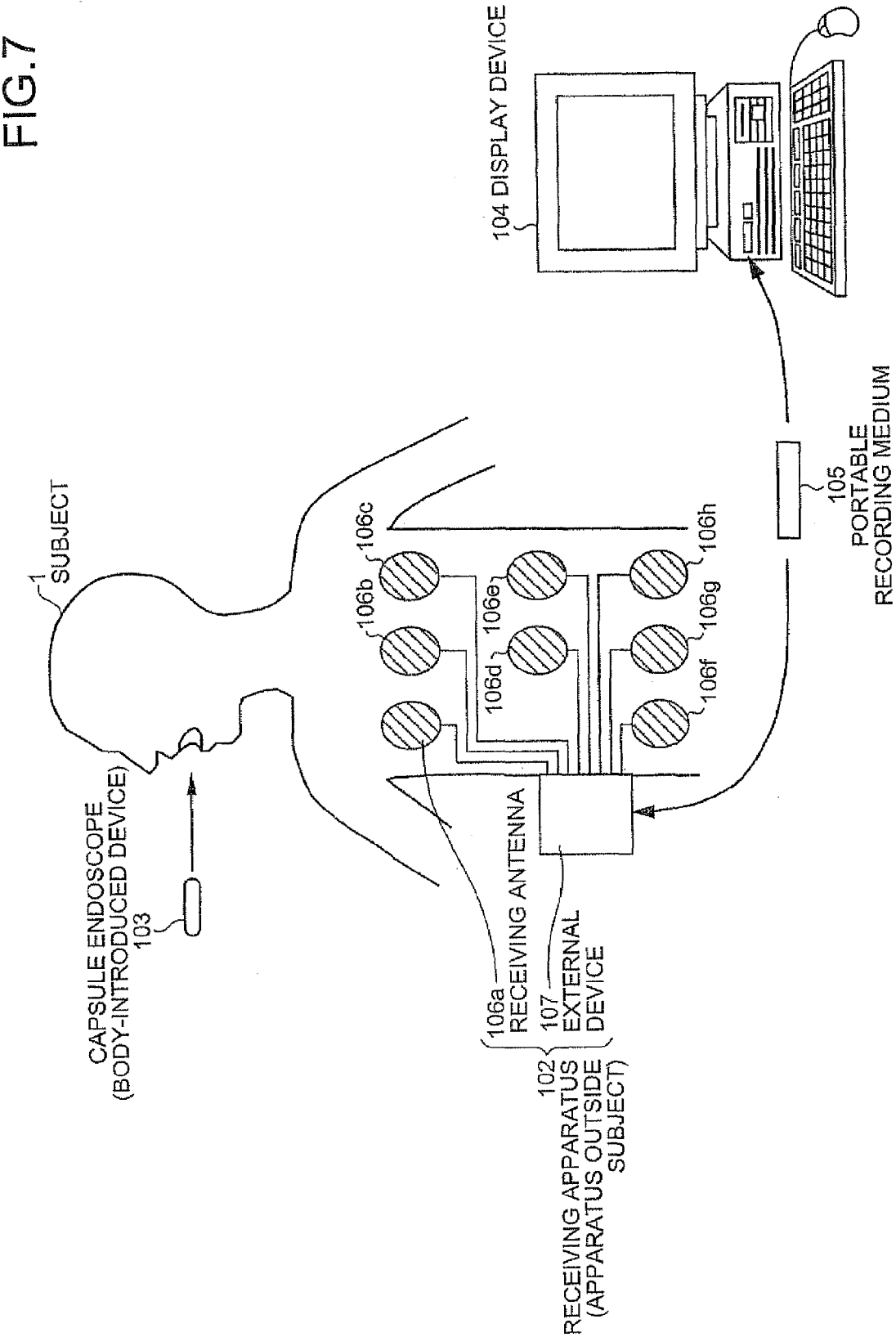
FIG. 7 is a schematic diagram showing the entire configuration of a body-introduced device system according to a third embodiment of the present invention.

FIG. 7 is a schematic diagram showing the entire structure of the body-introduced device system according to a third embodiment of the present invention. As shown in FIG. 7, the body-introduced device system includes a receiving apparatus 102 having radio receiving function and a capsule endoscope 103 which is introduced into a subject 101 in order to take the in vivo images of the subject and transmit data to the receiving apparatus 102. The body-introduced device system further includes a display device 104 which displays the in vivo image of the subject based on data which the receiving apparatus 102 receives and a portable recording medium 105 for exchanging data between the receiving apparatus 102 and the display device 104. The receiving apparatus 102 includes receiving antennas 106a to 106h and an external device 107 for performing predetermined processing on the radio signals received through the receiving antennas 106a to 106h.

The display device 104 is used for displaying images of the inside of the subject 101 taken by the capsule endoscope 103 and has a structure like a work station for displaying images based on data supplied through the portable recording medium 105. More specifically, the display device 104 may be configured to display images directly through CRT display or liquid crystal display or may be configured to output images to other medium like a printer.

The portable recording medium 105 is mounted detachably to the receiving apparatus 102 and the display device 104 and has a structure which enables output and recording of information when it is mounted to both of them. More specifically, the portable recording medium 105 is mounted to the receiving apparatus 102 while the capsule endoscope 103 is moved inside the cavity of the subject 101 so as to record information concerning the position of the capsule endoscope 103. More specifically, it is mounted to a memory unit (not shown) provided on the receiving apparatus 102 so as to acquire information through the memory unit. Then, after the capsule endoscope 103 is discharged out of the subject 101, the portable recording medium 105 is taken out of the receiving apparatus 102 and mounted to the display device 104 so that recorded data is read out by the display device 104. By exchanging data between the receiving apparatus 102 and the display device 104 through such a portable recording medium 105 as a CompactFlash (registered trademark) memory or the like, the subject 101 can move freely even if the capsule endoscope 103 is moved inside of the subject 101, contrary to a case where the receiving apparatus 102 and the display device 104 are connected by a wire.

Figure 8:
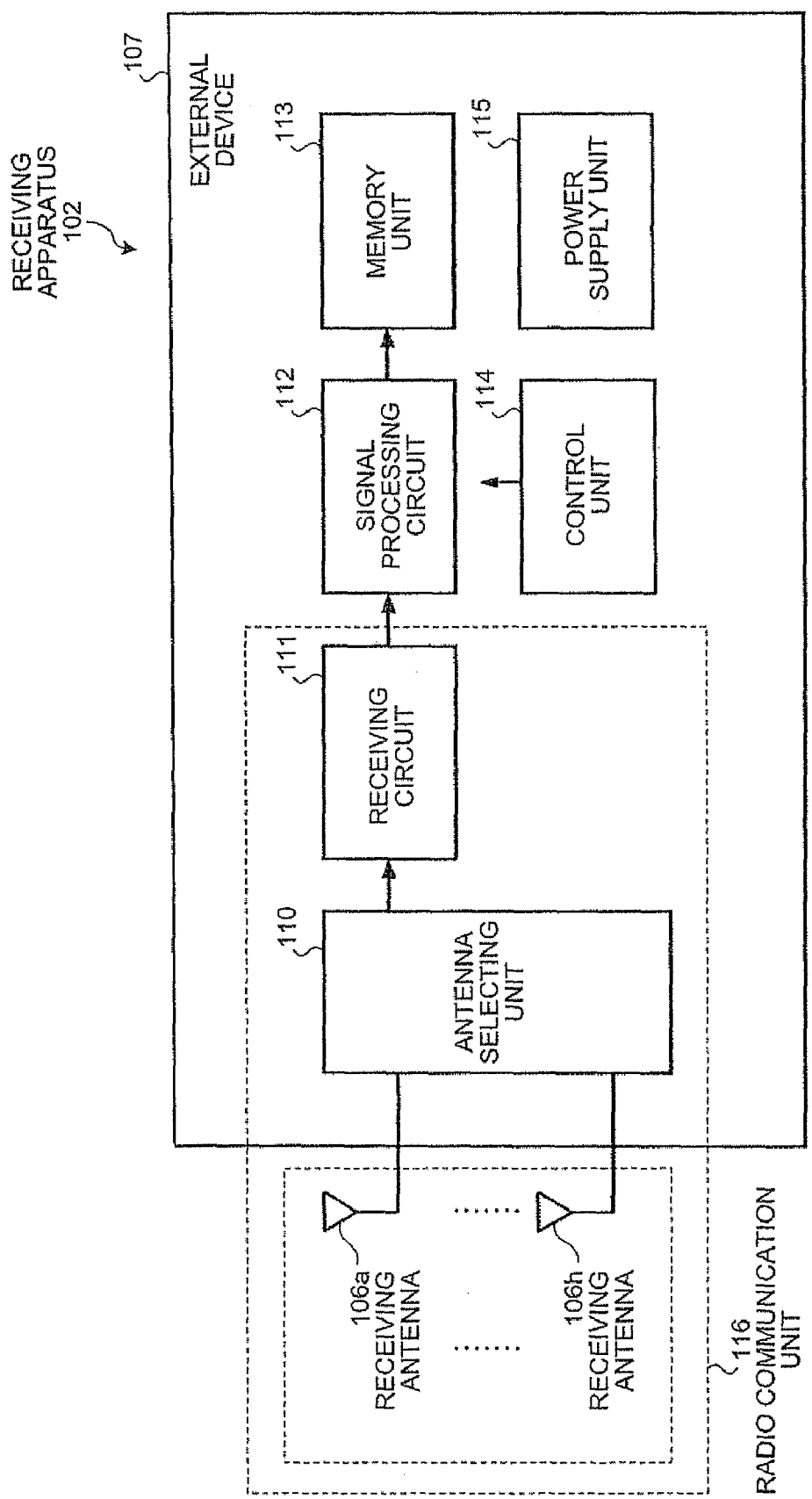
FIG. 8 is a block diagram showing the configuration of the receiving apparatus.

The receiving apparatus 102 communicates with the capsule endoscope 103 by radio and according to the third embodiment, receives a radio signal transmitted from the capsule endoscape 103, functioning as an example of the extra-subject unit. FIG. 8 is a block diagram showing the configuration of the receiving apparatus 102 and as shown in FIG. 8, the receiving apparatus 102 includes receiving antennas 106a to 106h and an external device 107.

The receiving antennas 106a to 106h are used while they are connected electrically with the external device 107 and disposed on the surface of the body of the subject 101 when in use and while the capsule endoscope 103 is introduced into the subject 10, receive a radio signal transmitted from the capsule endoscope 103. Although in the third embodiment, eight receiving antennas 106a to 106h are provided as an example, the number of the receiving antennas does not need to be interpreted to be limited to any particular one but it is permissible to use an arbitrary number of the receiving antennas as long as it is one or more.

The external device 107 includes an antenna selecting unit 110 which is connected to the receiving antennas 106a to 106h so as to select one appropriate for reception from the plurality of receiving antennas 106a to 106h, a receiving circuit 111 for performing demodulation processing on a radio signal received through a receiving antenna selected by the antenna selecting unit 110, a signal processing circuit 112 which performs a predetermined processing on a signal output from the receiving circuit 111, a memory unit 113 for memorizing data processed by the signal processing circuit 112 and a control unit 114 for controlling the respective components. The external device 107 includes a power supply unit 115 for supplying drive power to the above-mentioned respective components.

The antenna selecting unit 110 is connected to the plurality of the receiving antennas 106a to 106h so as to select any one of the receiving antennas 106a to 106h and output the radio signal received through a selected receiving antenna to the receiving circuit 111. More specifically, the antenna selecting unit 110 has a function of comparing the strength of radio signal received through each of the receiving antennas 106a to 106h and selecting a receiving antenna which receives the radio signal having the highest strength.

The receiving circuit 111 performs demodulation processing and the like on the radio signal output from the antenna selecting unit 110. The memory unit 113 stores predetermined information generated based on the radio signal which is transmitted from the capsule endoscope 103 and received through the receiving antennas 106a to 106h, or an image inside of the subject 101 in the example of the third embodiment. More specifically, the memory unit 113 has a function of outputting data to the portable recording medium 105. In the meantime, in the third embodiment, the receiving antennas 106a to 106h, the antenna selecting unit 110 and the receiving circuit 111 are generically called radio communication unit 116.

Next, the capsule endoscope 103 will be described. The capsule endoscope 103 functions as an example of the body-introduced device and is introduced into the subject 101 to execute a predetermined function to the subject 101 and performs radio communication with the receiving apparatus 102 disposed outside of the subject 101. More specifically, the capsule endoscope 103 has a function of taking pictures and transmitting the taken pictures to the receiving apparatus 102 by radio as predetermined functions.

Figure 9:
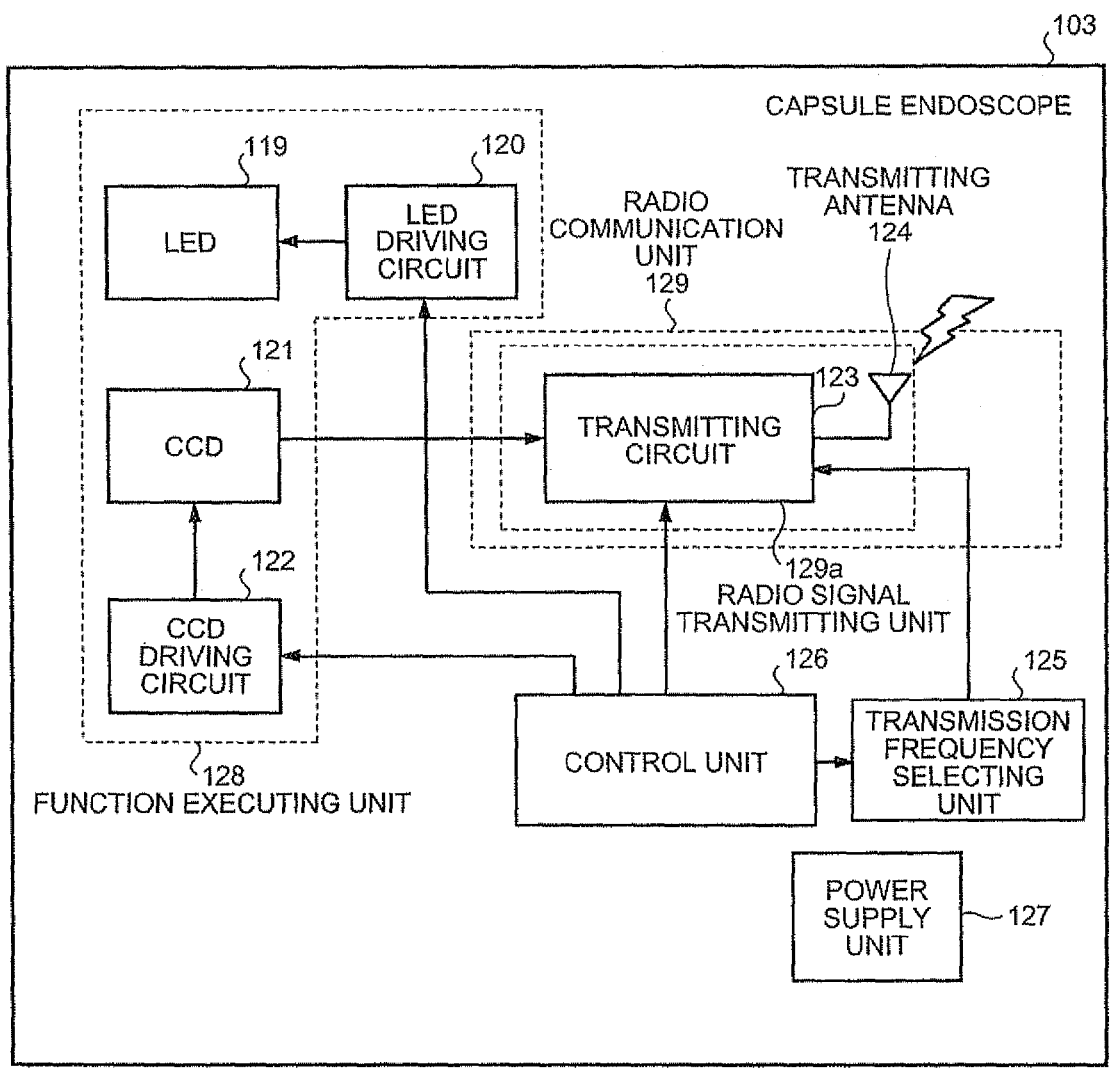
FIG. 9 is a block diagram showing the configuration of the capsule endoscope.

FIG. 9 is a block diagram showing the configuration of the capsule endoscope. As shown in FIG. 9, the capsule endoscope 103 includes an LED 119 which functions as an illuminating means for illuminating an image pickup area when the inside of the subject 101 is photographed, an LED driving circuit 120 for controlling the drive condition of the LED 119, a CCD 121 which functions as an image pickup means for photographing a reflection light image from an area illuminated by the LED 119 and a CCD driving circuit 122 for controlling the drive condition of the CCD 121. The LED 119, the LED driving circuit 120, the CCD 121 and the CCD driving circuit 122 as a whole operate as a function executing unit for performing a predetermined function. The capsule endoscope 103 includes a transmitting circuit 123 for generating a radio signal by modulating image data taken by the CCD 121, a transmitting antenna 124 for transmitting an RF signal output from the transmitting circuit 123 by radio, a transmission frequency selecting unit 125 which sets up the transmission frequency of a radio signal output by the transmitting circuit 123 changeably, a control unit 126 for controlling the drives of the LED driving circuit 120, the CCD driving circuit 122, the transmitting circuit 123 and the transmission frequency selecting unit 125 and a power supply unit 127 for supplying drive power to the respective components. In the third embodiment, the LED 119, the LED driving circuit 120, the CCD 121 and the CCD driving circuit 122 are generically called a function executing unit 128. Further, the transmitting circuit 123 and the transmitting antenna 124 are generically called radio signal transmitting unit 129a in the radio communication unit 129.

Figure 10:
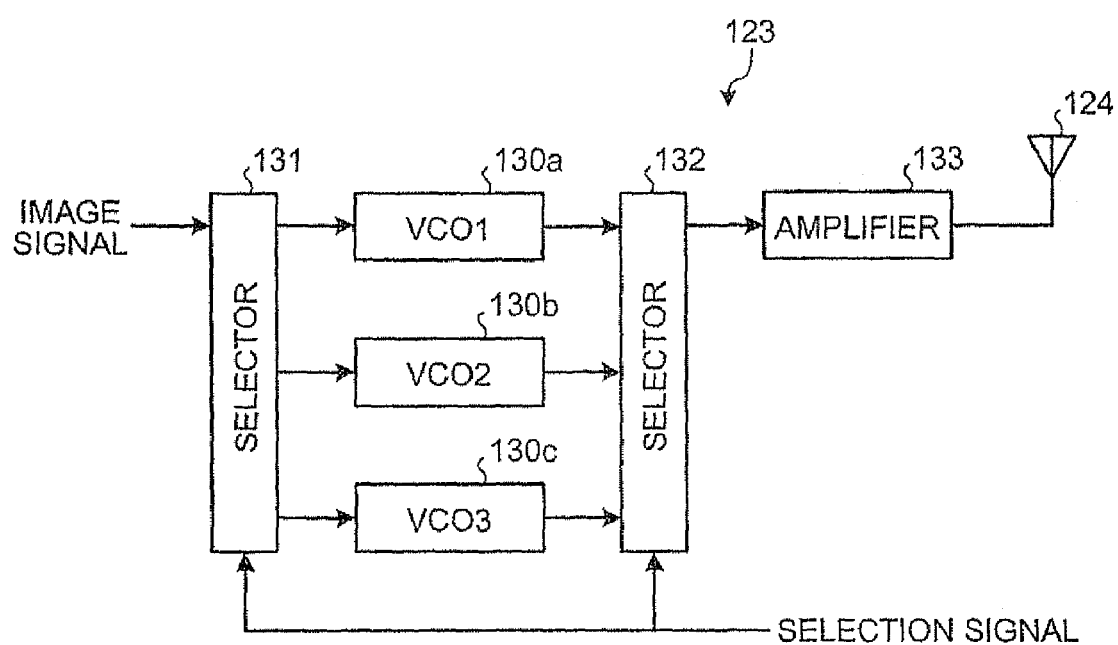
FIG. 10 is a block diagram showing an example of the configuration of a transmitting circuit.

The transmitting circuit 123 generates a radio signal having predetermined transmission frequency based on the image data taken by the CCD 121. Here, the transmitting circuit 123 has a configuration which can change the transmission frequency of a radio signal for use for communication and is changed corresponding to a selection signal from the transmission frequency selecting unit 125. FIG. 10 is a block diagram showing a configuration example of the transmitting circuit 123. As shown in FIG. 10, the transmitting circuit 123 includes plural, for example, three voltage control oscillators 130a, 130b, 130c represented with VCO1 to VCO3 for differentiating transmitting frequencies, a selector 131 which is located on the input side of the voltage control oscillators 130a to 130c and selects to which of the voltage control oscillators 130a to 130c image signal from the CCD 121 is to be input corresponding to a selecting signal, a selector 132 which is located on the output side of the voltage control oscillators 130a to 130c and selects which transmission frequency signal is to be output corresponding to a selection signal and an amplifier 133 for amplifying an image signal of a transmission frequency selected by the selector 132. In the meantime, although the third embodiment is described such that it has for example three voltage control oscillators 130a to 130c for simplification of description, the number of the voltage control oscillators does not need to be interpreted so as to be limited to any particular number and it is permissible to use any number of the voltage control oscillators as long as it is one or more.

The transmission frequency selecting unit 125 which functions as a frequency setting means selects the transmission frequency of a radio signal output from the transmitting circuit 123 to any one specified by the voltage control oscillators 130a to 130c and, in the third embodiment, outputs a selection signal set preliminarily corresponding to a usage area or the like for each of the capsule endoscopes 103 to the selectors 131, 132. Thus, in a certain usage area, the transmission frequency selecting unit 125 outputs a selection signal to select the voltage control oscillator (VCO1) 130a to the selectors 131, 132 and the capsule endoscope 103 outputs an image signal from the CCD 121 from the transmitting antenna 124 as a radio signal of transmission frequency determined by the voltage control oscillator (VCO1) 130a. Likewise, in another certain usage area, the transmission frequency selecting unit 125 outputs a selection signal for selecting the voltage control oscillator (VCO2) 130b to the selectors 131, 132 and the capsule endoscope 103 outputs an image signal from the CCD 121 from the transmitting antenna 124 as a radio signal having a transmission frequency determined by the voltage control oscillator (VCO2). Further, in still another certain usage area, the transmission frequency selecting unit 125 outputs a selection signal for selecting the voltage control oscillator (VCO3) 130c to the selectors 131, 132 and the capsule endoscope 103 transmits an image signal from the CCD 121 from the transmitting antenna 124 as a radio signal having a transmission frequency determined by the voltage control oscillator (VCO3) 130c.

Because the capsule endoscope 103 of the third embodiment is capable of changing the transmission frequency of a radio signal for use in communication and the transmission frequency is set changeably by the transmission frequency selecting unit 125, by setting the selection signal which the transmission frequency selecting unit 125 selects preliminarily corresponding to a usage area or the like, the capsule endoscopes 103 having plural kinds of structures each selecting a different transmission frequency depending on a destination place by taking into account the usage area do not need to be manufactured, so that there is an advantage that the capsule endoscopes 103 having the same structure can be used appropriately at plural places.

Figure 11:
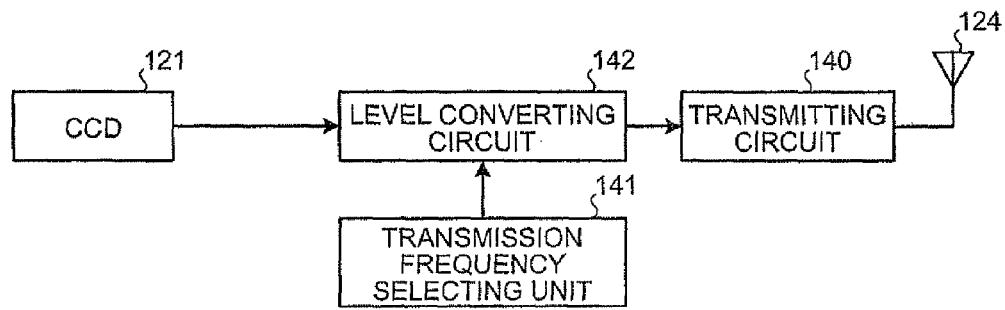
FIG. 11 is a schematic block diagram showing a first modification for varying the transmission frequency of the capsule endoscope.
Figure 12:
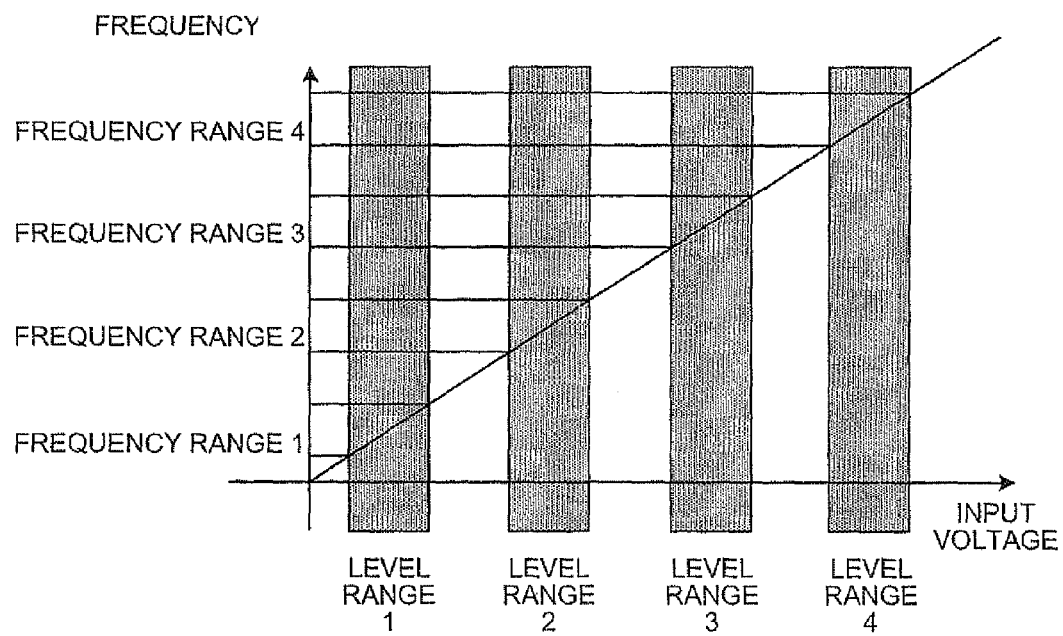
FIG. 12 is a conversion characteristic diagram showing the varying method of FIG. 11.

Although according to the third embodiment, the capsule endoscope 103 is capable of changing the transmission frequency freely using the plurality of voltage control oscillators 130a to 130c, the transmission frequency may be changed by other methods. FIG. 11 is a schematic block diagram showing a first modification for changing the transmission frequency of the capsule endoscope 103 and FIG. 12 is a conversion characteristic diagram showing the changing method. The capsule endoscope 103 of the modification 1 includes a transmitting circuit 140 for outputting a radio signal at a transmission frequency corresponding to the level of input voltage and a level converting circuit 142 which is provided on a prestage of this transmitting circuit 140 so as to vary the level of the input voltage to the transmitting circuit 140 corresponding to a selection signal indicating a frequency range from the transmission frequency selecting unit 141.

According to the first modification, as shown in FIG. 12 for example, four stages of discrete frequency selection signals indicated by frequency ranges 1 to 4 are prepared in the transmission frequency selecting unit 141 and the level converting circuit 142 is set so as to change the level of the input voltage to discrete values of four stages indicated by level ranges 1 to 4 corresponding to each frequency selection signal. According to the first modification, the transmission frequency selecting unit 141 outputs a frequency selection signal set preliminarily corresponding to the usage area or the like for each capsule endoscope 103 to the level converting circuit 142.

To change the transmission frequency of a radio signal output by the capsule endoscope 103, the transmitting antenna 124 includes a parallel resonance circuit comprising a coil and a variable capacity capacitor capable of changing the electrostatic capacity value and the electrostatic capacity value of the variable capacity capacitor may be set variably based on a control of the frequency setting unit. When the electrostatic capacity value of the variable capacity capacitor is changed, the resonance frequency of the parallel resonance circuit formed of the coil and variable capacity capacitor changes. Consequently, by adjusting the electrostatic capacity value of the variable capacity capacitor, a radio signal having a transmission frequency set by the frequency setting unit 7 can be transmitted.

Next, the body-introduced device system of a fourth embodiment will be described. The body-introduced device system of the fourth embodiment has a function of searching for an unused channel by sweeping a reception frequency at a usage place by a receiving apparatus and determining the transmission frequency for the capsule endoscope based on the searched unused channel so as to transmit to the capsule endoscope and a structure in which the capsule endoscope changes the transmission frequency of the radio signal by receiving this determined transmission frequency.

Figure 13:
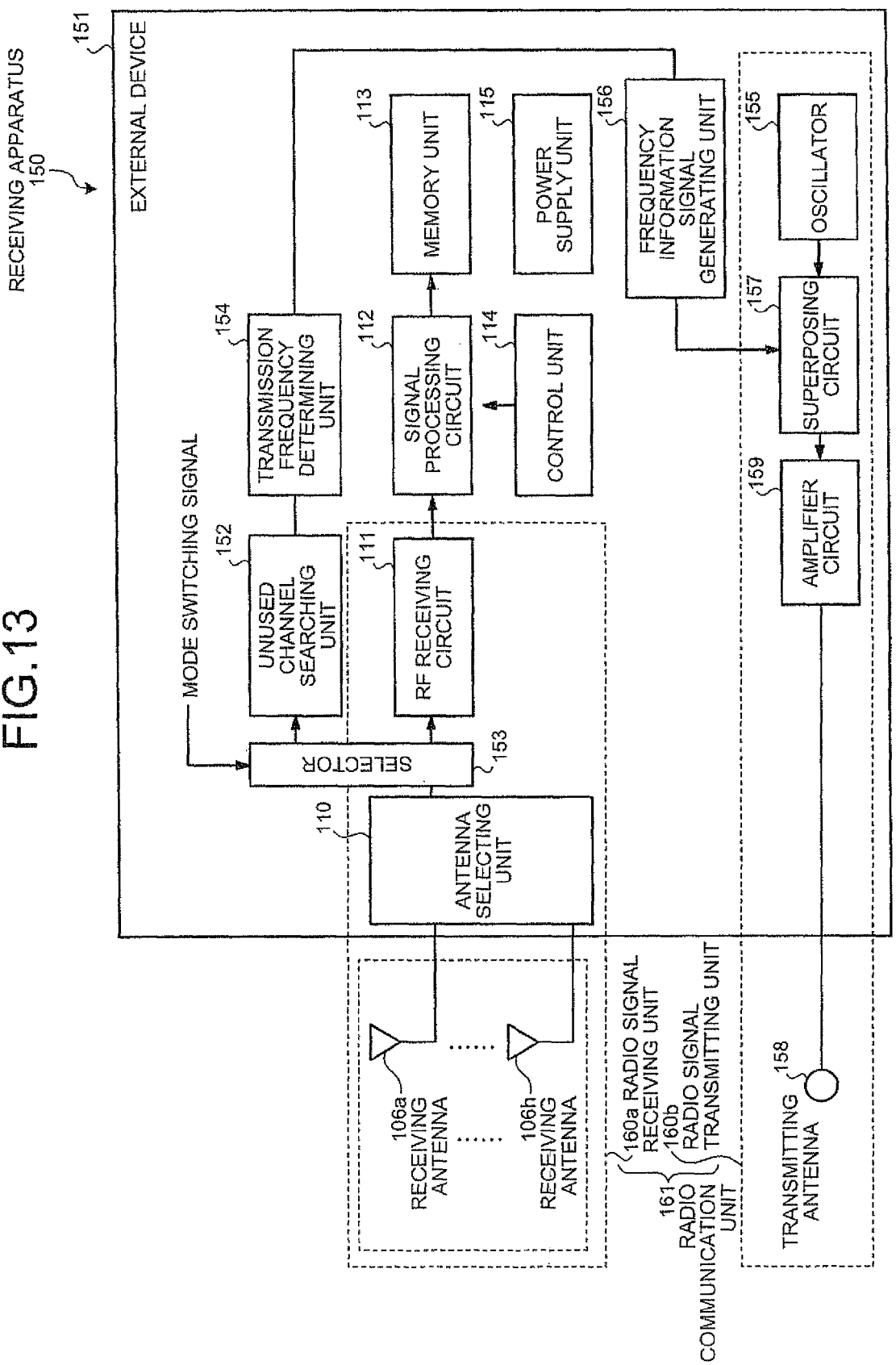
FIG. 13 is a block diagram showing the configuration of the receiving apparatus in the body-introduced device system according to a fourth embodiment of the present invention.

FIG. 13 is a block diagram showing the configuration of the receiving apparatus equipped on the body-introduced device system according to the fourth embodiment. As shown in FIG. 13, a receiving apparatus 150 includes receiving antennas 106a to 106h like the third embodiment and an external device 151 includes the antenna selecting unit 110, the receiving circuit 111, the signal processing circuit 112, the memory unit 113, the control unit 114, and the power supply unit 115. On the other hand, the receiving apparatus 150 of the fourth embodiment has a function of searching for an unused channel by sweeping the reception frequency at a place where this receiving apparatus 150 is used, determining the transmission frequency for the capsule endoscope 103 based on the unused channel and transmitting to the capsule endoscope 103.

More specifically, the external device 151 includes an unused channel searching unit 152 for searching for an unused channel by sweeping the receiving frequency of the radio signal at the place where the receiving apparatus 150 is used, a selector 153 for selecting whether any reception signal through the antenna selecting unit 110 should be output to the RF receiving circuit 111 or the unused channel searching unit 152 based on a mode selecting signal, a transmission frequency determining unit 154 for determining the transmission frequency which the capsule endoscope 103 uses for radio communication based on an unused channel searched by the unused channel searching unit 152, an oscillator 155 for generating a signal for specifying the transmission frequency, a frequency information signal generating unit 156 for generating frequency information signal included in the radio signal to be transmitted to the capsule endoscope 103 based on the determined transmission frequency, a superposing circuit 157 for synthesizing the generated frequency information signal with a signal generated by the oscillator 155 and an amplifier circuit 159 which amplifies the strength of a signal synthesized by the superposing circuit 157 and outputs to the transmitting antenna 158 as well as the above-described structure. In the meantime, in the fourth embodiment, the receiving antennas 106a to 106h, the antenna selecting unit 110 and the receiving circuit 111 are generically called a radio signal receiving potion 160a and the oscillator 155, the superposing circuit 157, the amplifier circuit 159 and the transmitting antenna 158 are generically called a radio signal transmitting unit 160b. Further, the radio receiving unit 160a and the radio transmitting unit 160b are generically called a radio communication unit 161.

Figure 14:
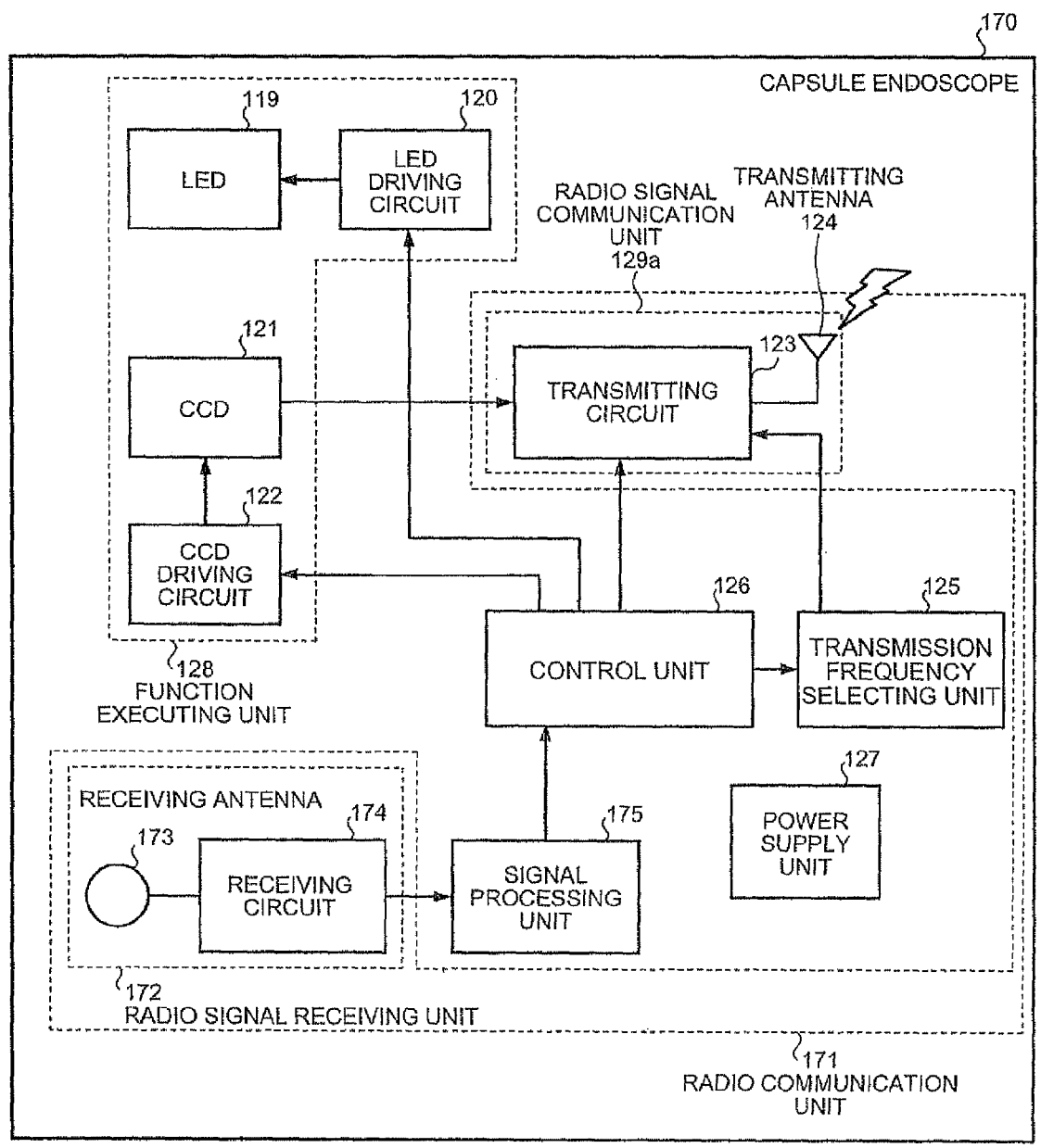
FIG. 14 is a block diagram showing the configuration of the capsule endoscope according to a fourth embodiment of the present invention.

Next, the configuration of the capsule endoscope according to the fourth embodiment will be described. FIG. 14 is a block diagram showing the configuration of the capsule endoscope according to the fourth embodiment. As shown in FIG. 14, the capsule endoscope 170 includes the function executing unit 128 like the third embodiment and has a structure having a radio communication unit 171 having a radio signal transmitting/receiving function. The radio communication unit 171 has a structure including a radio signal receiving unit 172 for setting the transmission frequency based on an external input in addition to the structure of the third embodiment and the radio signal receiving unit 172 is equipped with a receiving antenna 173 and a receiving circuit 174 for demodulating a radio signal received through and the receiving antenna 173.

The capsule endoscope 170 includes a signal processing unit 175 which extracts a frequency information signal concerning the transmission frequency included in a radio signal by performing predetermined processing on a signal output from the receiving circuit 174 and outputs the extracted frequency information signal to the control unit 126 and a transmission frequency selecting unit 125 for outputting a selection signal for selecting the transmission frequency output by the transmitting circuit 123 based on the frequency information signal input into the control unit 126. In other words, the transmission frequency selecting unit 125 of the fourth embodiment outputs a selection signal for setting the transmission frequency to the transmitting circuit 123 based on an instruction from the receiving apparatus 150 side which is an external input. The transmitting circuit 123 changes the frequency so as to output a radio signal of transmission frequency selected corresponding to a selection signal from the transmission frequency selecting unit 125.

Figure 15:
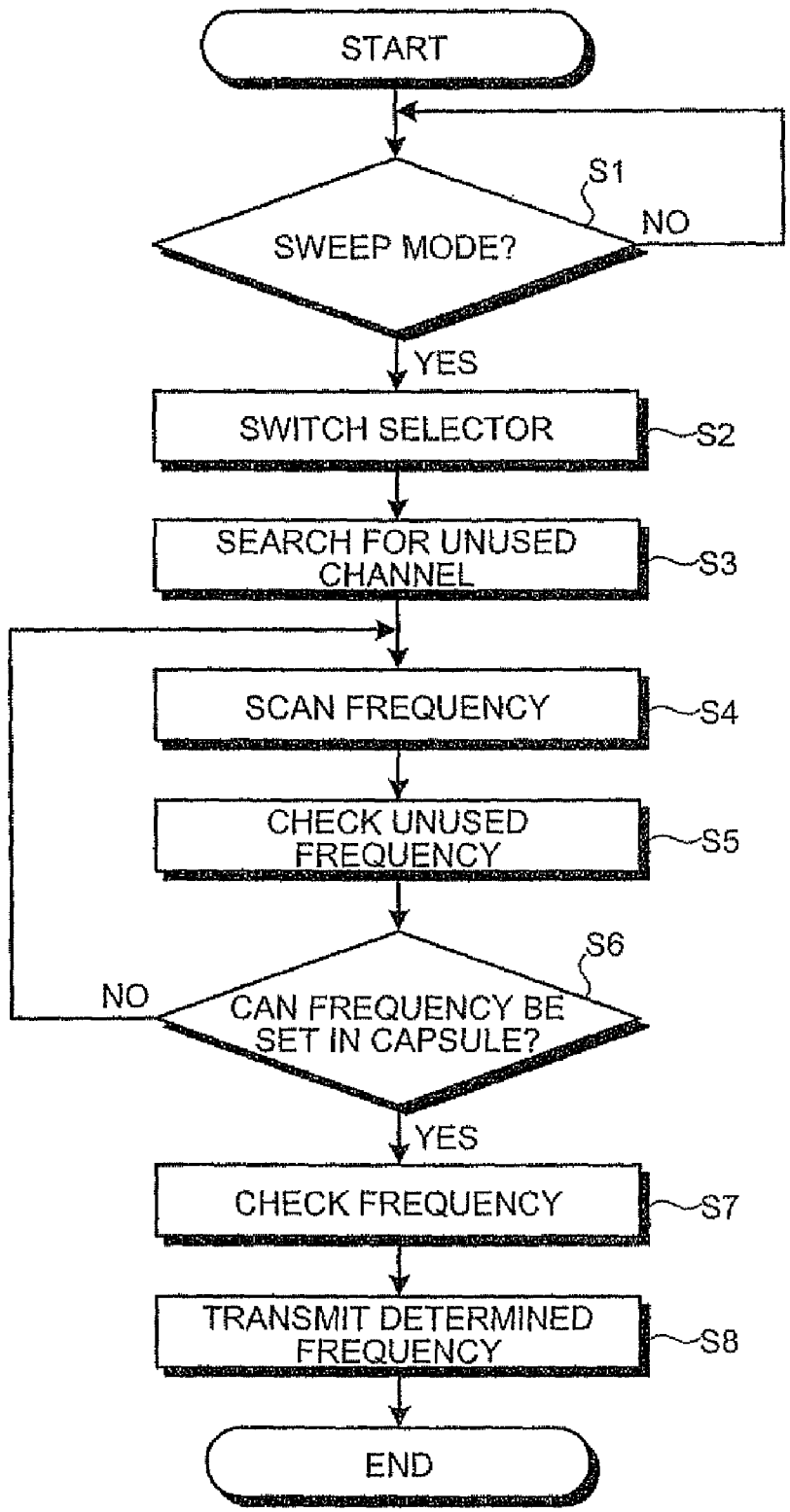
FIG. 15 is a schematic flow chart for explaining decision of a transmission frequency and transmitting operation.

Next, operations for determining and setting the transmission frequency of the capsule endoscope 170 in the body-introduced device system of the fourth embodiment will be described. FIG. 15 is a schematic flow chart for explaining the operations for determining and transmitting the transmission frequency to be executed by the unused channel searching unit 152, the transmission frequency determining unit 154, the frequency information generating unit 156 and the radio signal transmitting unit 160b under a control by the control unit 114.

This processing is carried out by setting the receiving apparatus 150 to sweep mode at the usage place (for example, within a hospital) prior to using the body-introduced device system for actual purposes (step S1: Yes). When it is set to sweep mode, the control unit 114 changes the output side of the selector 153 to the unused channel searching unit 152 side (step S2). Then, unused channel searching operation by the unused channel searching unit 152 is executed (step S3) and by executing frequency scan for varying the receiving frequency of the receiving apparatus 150 in a predetermined frequency step (step S4), an unused channel is searched by sweeping at a receiving frequency (step S5). This processing is repeated until a frequency corresponding to an unused channel which can be set as the transmission frequency of the capsule endoscope 170 is found (step S6). If the frequency corresponding to an appropriate unused channel is found (step S6: YES), it is determined as the transmission frequency which the capsule endoscope 170 uses at a given place by the transmission frequency determining unit 154 (step S7). Then, the frequency information signal generating unit 156 and the radio signal transmitting unit 160b output frequency information signal including information about the determined transmission frequency from the transmitting antenna 158 to the capsule endoscope 170 (step S8).

The capsule endoscope 170 receives a radio signal including frequency information signal transmitted from the transmitting antenna 158 of the receiving apparatus 150 through the receiving antenna 173 and the signal processing unit 175 extracts frequency information signal concerning the determined transmission frequency included in the radio signal. The control unit 126 sets a selection signal corresponding to this frequency information signal in the transmission frequency selecting unit 125 and the transmission frequency selecting unit 125 makes the transmitting circuit 123 perform selecting operation for the transmission frequency so as to output a radio signal of the transmission frequency determined by the receiving apparatus 150.

The body-introduced device system of the fourth embodiment searches for an unused channel different depending on the usage place by sweeping the receiving frequency of a radio signal at an actual usage place and determines the transmission frequency for the capsule endoscope 170 based on the searched unused channel. The capsule endoscope 170 can use the transmission frequency in a frequency band not interfered with by other electronic devices without interfering with other electronic devices by using the transmission frequency corresponding to this determined unused channel. Consequently, capsule endoscopes having different kinds of structures in which the transmission frequency is changed for each destination place by taking into account the usage area do not need to be manufactured, so that the capsule endoscope 170 having the same structure can be used appropriately at plural places.

Figure 16:
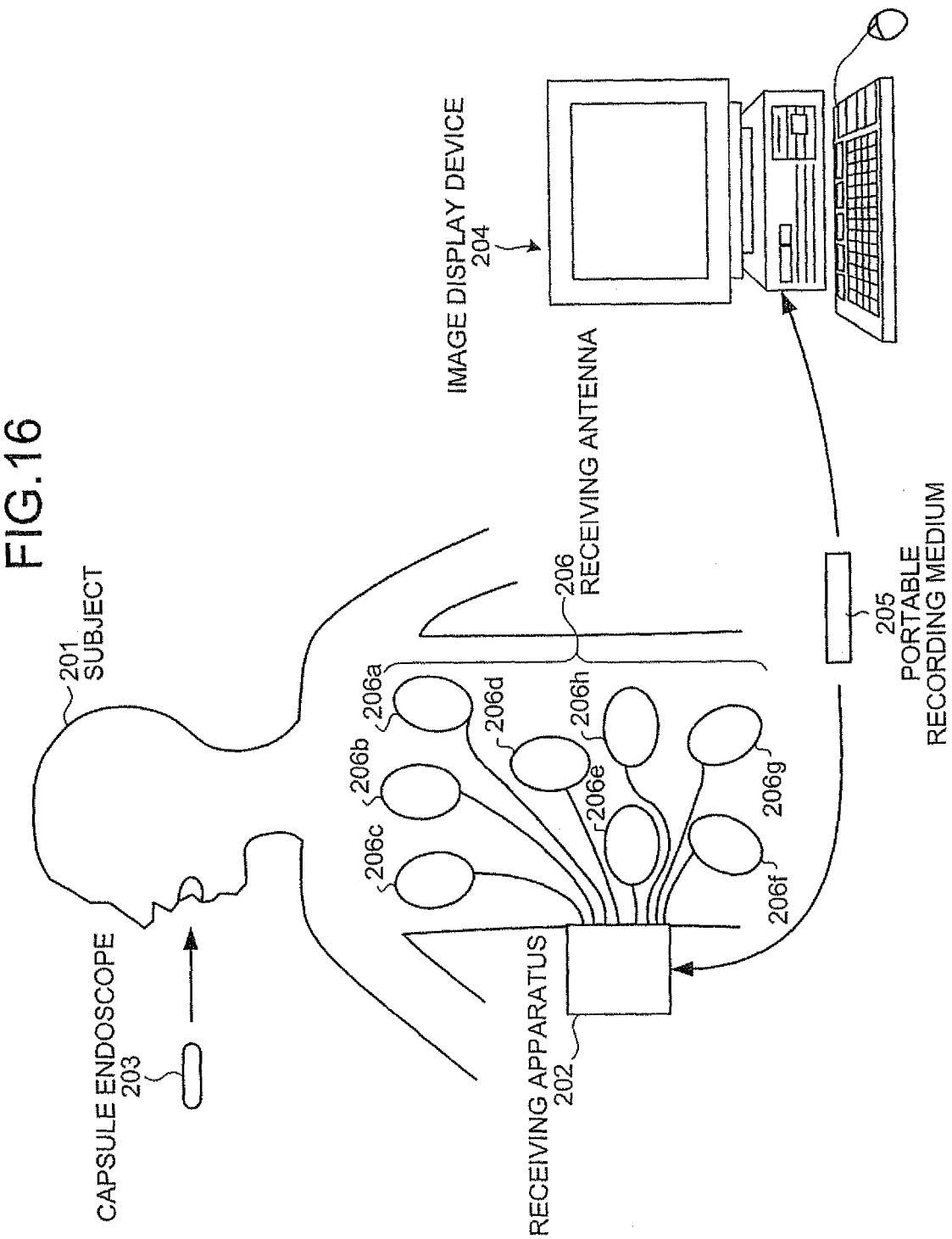
FIG. 16 is a schematic diagram showing the entire configuration of a radio-type intra-subject information acquiring system including the receiving apparatus of a fifth embodiment of the present invention.

First, the radio-type intra-subject in vivo information acquiring system having the receiving apparatus according to a fifth embodiment will be described. FIG. 16 is a schematic diagram showing the entire structure of the radio-type intra-subject in vivo information acquiring system. This radio-type intra-subject in vivo information acquiring system uses the capsule endoscope as an example of the body-introduced device.

As shown in FIG. 16, the radio-type intra-subject in vivo information acquiring system is introduced into the inside of the subject 201 and includes a capsule endoscope 203 which transmits image data of the taken subject in vivo image to a receiving apparatus 202 by radio, the receiving apparatus 202 for receiving image data transmitted from the capsule endoscope 203 by radio, an image display device 204 which displays the subject in vivo image based on the image signal received by the receiving apparatus 202, and a portable recording medium 205 for exchanging image data and the like between the receiving apparatus 202 and the image display device 204.

The receiving apparatus 202 has a receiving antenna 6 having a plurality of antennas 206a to 206h which are to be affixed to the surface of the body of the subject 201. The receiving apparatus 202 receives image data and the like transmitted by radio from the capsule endoscope 203 through the receiving antenna 6. The antennas 206a to 206h are achieved using for example, loop antenna and disposed at positions corresponding to each organ inside the subject 201 which is a predetermined position on the surface of the subject 201, that is, a passage through which the capsule endoscope 203 passes.

In the meantime, the antennas 206a to 206h may be disposed at predetermined positions of a jacket or the like which the subject 201 wears. In this case, the antennas 206a to 206h are disposed at the predetermined positions on the outside surface of the subject 201 through this jacket or the like. The arrangement positions of the antennas 206a to 206h can be changed arbitrarily corresponding to the purpose for observation and diagnosis for the inside of the subject 201. In the meantime, the number of antennas provided on the receiving antennas 6 does not need to be interpreted to be limited to eight indicated with the antennas 206a to 206h but may be smaller or larger than eight.

The image display device 204 is achieved as a work station provided with for example, CRT, liquid crystal display and the like and displays images based on the image data acquired through the portable recording medium 205 and the like. The image display device 204 can output and display image data to an output device such as a printer. In the meantime, the image display device 204 may be provided with communication function with an outside device so that image data may be acquired or output by wired or wireless communication.

The portable recording medium 205 is realized with a CompactFlash memory (registered trademark) memory, CD, DVD and the like and can be mounted detachably to the receiving apparatus 202 and the image display device 204. When it is mounted to these, various kinds of information such as image data can be output or recorded. The portable recording medium 205 is mounted to the receiving apparatus 202 while the capsule endoscope 203 is introduced into the subject 201 and the receiving apparatus 202 records image data and the like received from the capsule endoscope 203. After the capsule endoscope 203 is discharged out of the subject 201, it is taken out of the receiving apparatus 202 and mounted to the image display device 204 so that recorded image data is output to the image display device 204.

By exchanging image data between the receiving apparatus 202 and the image display device 204 through the portable recording medium 205, the subject 201 can move freely even when the capsule endoscope 203 is introduced. The exchange of data between the receiving apparatus 202 and the image display device 204 may be carried out by wired or wireless communication.

Figure 17:
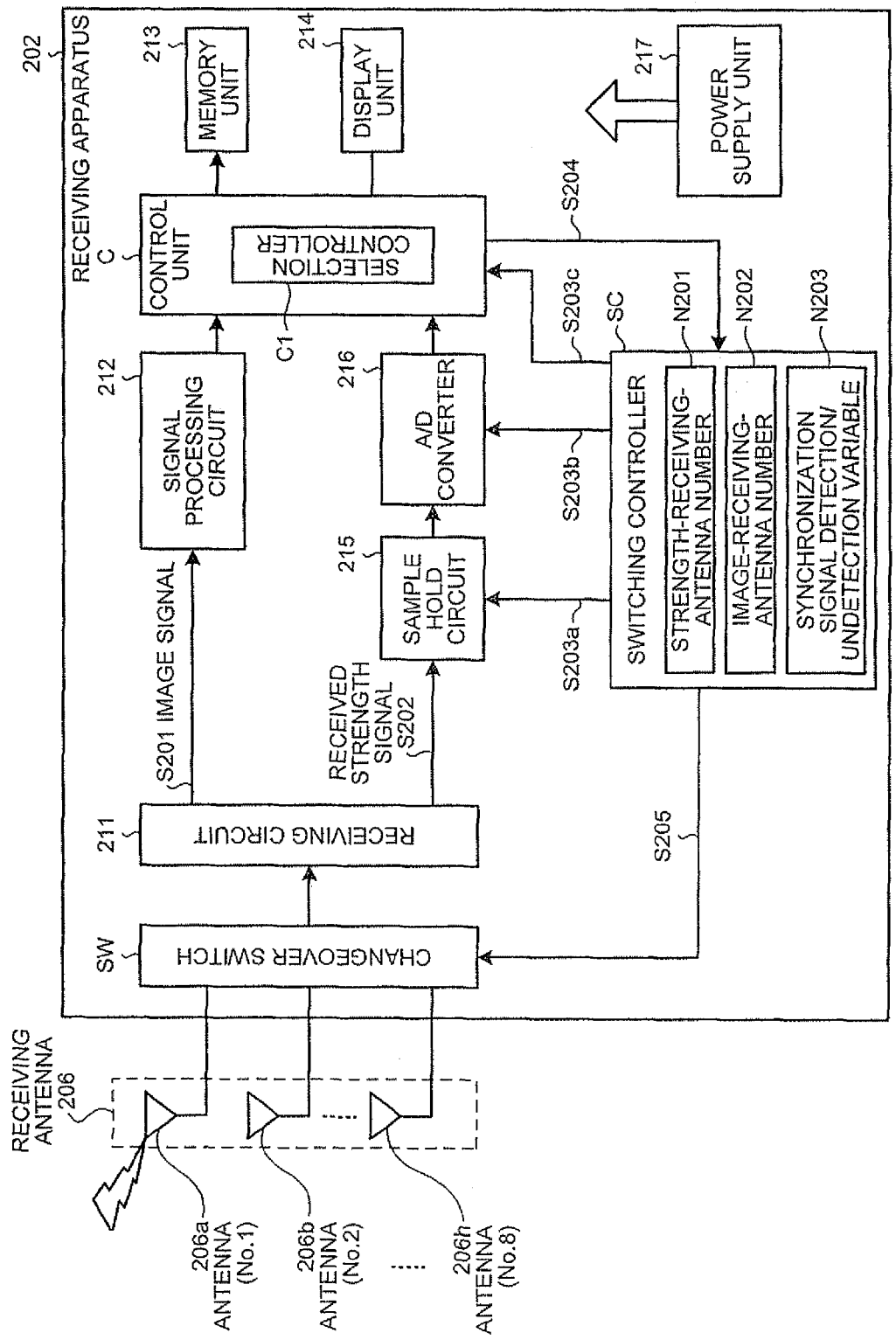
FIG. 17 is a block diagram showing the configuration of the receiving apparatus shown in FIG. 16.

Here, the receiving apparatus 202 will be described with reference to FIG. 17. FIG. 17 is a block diagram showing the configuration of the receiving apparatus 202. As shown in FIG. 17, the receiving apparatus 202 has a function of processing a radio signal transmitted from the capsule endoscope 203. More specifically, as shown in FIG. 17, the receiving apparatus 202 includes a changeover switch SW for switching connection of the antennas 206a to 206h each having a series of antenna numbers and a receiving circuit 211 which is connected to a poststage of the changeover switch SW so as to amplify and demodulate radio signals from the antennas 206a to 206h connected switchably by the changeover switch SW and a signal processing circuit 212 and a sample hold circuit 215 are connected to the poststage of the receiving circuit 211. An A/D converter 216 is connected to the post stage of the sample hold circuit 215.

The control unit C has a selection control unit C1 and a signal processing circuit 212, A/D converter 216, memory unit 213 corresponding to the portable recording medium 205, display unit 214 and switching controller SC are connected thereto. The switching controller SC includes strength-receiving-antenna number N201, image-receiving-antenna number N202, and synchronization signal detection/undetection variable N203 and instructs switching of the changeover switch SW based on these information while instructing processing timing of the sample hold circuit 215, A/D converter 216 and selection controller C1. The power supply unit 217 supplies electricity to the respective components and is achieved for example by a battery.

The changeover switch SW of the receiving apparatus 202 switches the antennas 206a to 206h selectively according to a switching instruction from the switching controller SC and outputs a radio signal from the selected antenna 206a to 206h to the receiving circuit 211. The receiving circuit 211 amplifies the radio signal as described above, outputs the demodulated image signal S201 to the signal processing circuit 212 and outputs received strength signal S202 indicating the reception electric field strength of the amplified radio signal to the sample hold circuit 215. Image data processed by the signal processing circuit 212 is stored in the memory unit 213 by the control unit C and output and display by the display unit 214.

A signal sample-held by the sample holding circuit 215 is converted to a digital signal by the A/D converter 216 and taken into the control unit C. The selecting controller C1 of the control unit C compares the electric field strength received in a strength receiving period described later with an electric field strength received in image signal period and if the electric strength received in the strength receiving period exceeds the electric field strength received in the image signal period, a receiving antenna selected in this strength receiving period is selected as a receiving antenna in the image signal period and receiving antennas other than this selected receiving antenna are selected successively as a receiving antenna in the strength receiving period while the other receiving antenna numbers are output to the switching controller SC as a signal S204 having image-receiving-antenna number N202 and strength-receiving-antenna number N201.

The switching controller SC holds the strength-receiving-antenna number N201 and image-receiving-antenna number N202 instructed by the selection controller C1, instructs the changeover switch SW so as to connect the antennas 206a to 206h corresponding to the strength-receiving-antenna number N201 selectively in the strength receiving period, outputs a signal S205 for instructing the changeover switch SW so as to connect the antennas 206a to 206h corresponding to the image-receiving-antenna number N202 selectively in the image signal period to the changeover switch SW and then, outputs signal S203a for instructing sample hold timing by the sample holding circuit 215, signal S203b for instructing A/D conversion timing by the A/D converter 216 and a signal s203c for instructing selection control timing by the selection controller C1.

Figure 18:
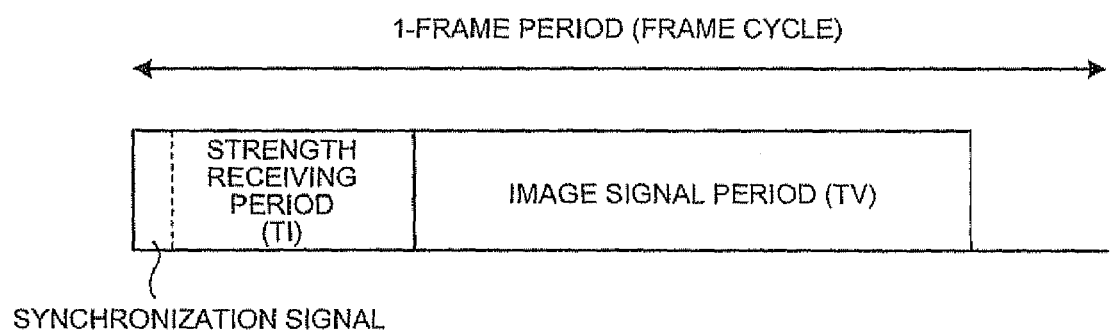
FIG. 18 is a diagram showing the frame format of a radio signal transmitted from the capsule endoscope shown in FIG. 16.

Here, the strength receiving period and image signal period, i.e., the configuration of the frame for a radio signal will be described with reference to FIGS. 18 and 19. The outline of the selection switching processing of the antennas 206a to 206h will be described. The radio signal transmitted from the capsule endoscope 203 is transmitted in the frame unit and this frame unit includes the strength receiving period (TI) and image signal period (TV) as shown in FIG. 18. The strength receiving period is a period corresponding to a preamble signal period for reception adjustment and a synchronization signal indicating a transmitting timing from the capsule endoscope 203 is included at the head of this period. Further, the image signal period may include control signal necessary for receiving image signal as well as the image signal.

Figure 19:
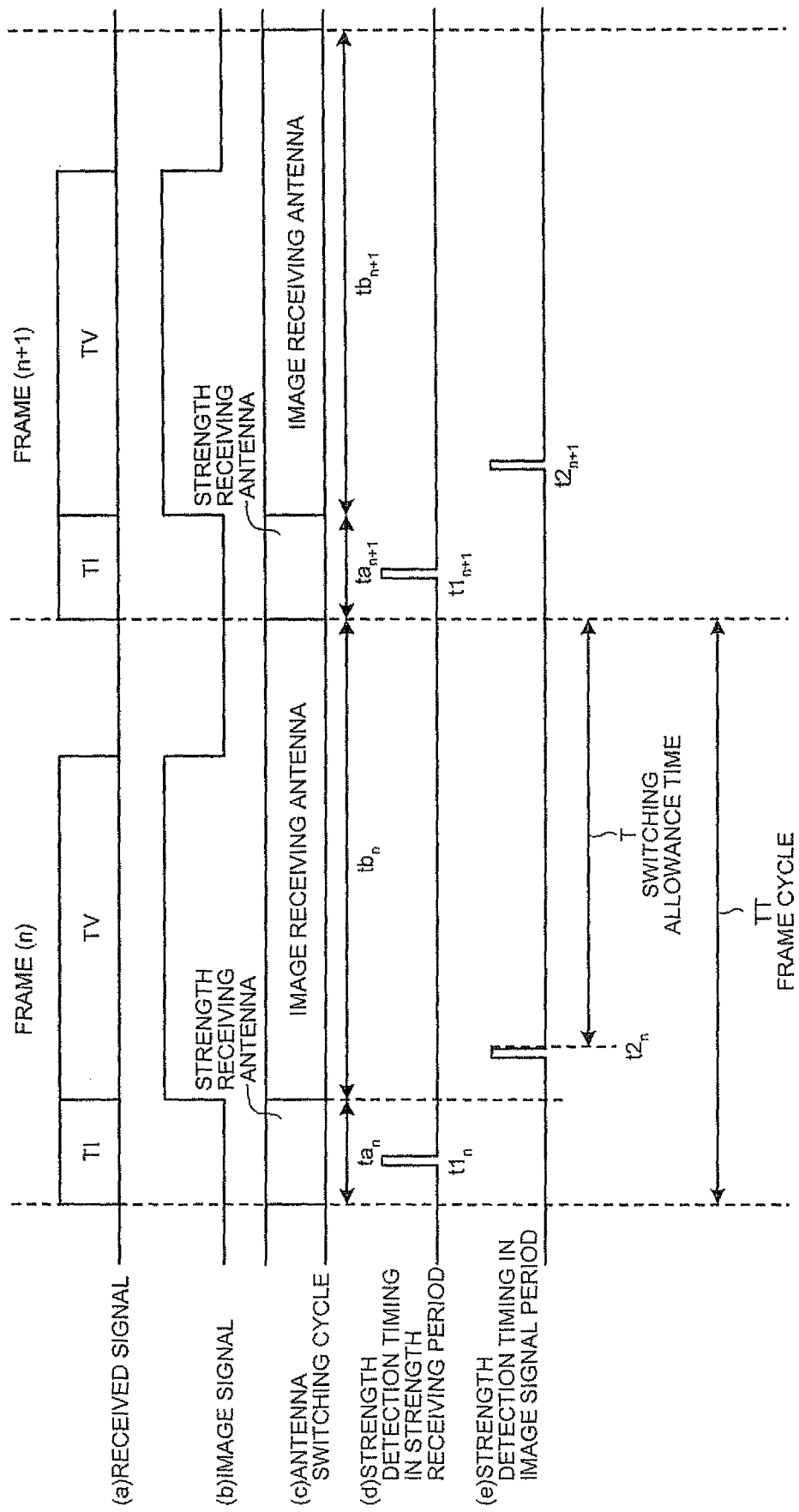
FIG. 19 is a time chart showing received electric field strength measuring processing of each frame of the receiving apparatus shown in FIG. 16.

Each frame is transmitted as shown in FIG. 19 and sometimes a non-signal condition exists between the respective frames while sometimes the frames are transmitted continuously. The frame cycle TT for frame transmitting is set short in an image pick area of note or in an area in which the capsule endoscope 203 is moved rapidly by considering effective use of the battery of the capsule endoscope 203 and the length of the frame cycle TT is adjusted flexibly to be longer or shorter.

As shown in FIG. 19, if an n-th frame (n) and a (n+1)-th frame (n+1) are transmitted successively, the receiving antenna (image receiving antenna) for receiving in the image signal period (TV) of the same frame (n) is switched to other receiving antenna (strength receiving antenna) in a period $ta_n$ corresponding to the strength receiving period (TI) of the frame (n) and in a period $tb_n$ including the image signal period and an interval until a start of the strength receiving period of a next frame (n+1), the image receiving antenna is selected. Likewise, in a period $ta_{n+1}$ corresponding to the strength receiving period of the frame (n+1), the strength receiving antenna of the same frame (n+1) is selected and then, in a period $tb_{n+1}$ including the image signal period and an interval until a start of the strength receiving period of a next frame (n+2), the image receiving antenna is selected.

Further, at a timing $t1_n$ in the strength receiving period of the frame (n), strength detection processing by the sample holding circuit 215 and the A/D converter 216 is executed and its result is output to the selection controller C1. Likewise, at a timing $t2_n$ in the image signal period of the frame (n), the strength detection processing by the sample holding circuit 215 and the A/D converter 216 is executed and its result is output to the selection controller C1.

Thus, an allowance period until the antenna switching processing of the next frame (n+1) becomes a switching allowance time T from this timing $t2_n$ until a start of the strength receiving period of the next frame (n+1). Thus, by shifting the timing $t2_n$ to an early timing of the image signal period, the switching allowance time T can be increased. If this switching allowance time T is increased, the high speed performance of the sample holding circuit 215, A/D converter 216, selection switching controller C1, switching controller SC and changeover switch SW become unnecessary thereby the system being achieved with a simple circuit unit.

Further, the receiving electric field strength of the receiving antenna for receiving image signal is received and measured in the image signal period and it does not need to be measured in the strength receiving period, whereby eliminating the necessity of switching the antenna quickly. When the receiving electric field strength of the plurality of receiving antennas is measured in the strength receiving period, the receiving electric field strength of the image signal does not need to be measured, thereby providing the switching operation with an allowance.

By the way, the selection switching processing between the strength receiving antenna and the image receiving antenna shown in FIG. 19 can be executed in case where the transmitting signal from the capsule endoscope 203 is synchronous with the strength detection timing in the receiving apparatus 202, that is, the timing $t1_n$ is included in the period $ta_n$ corresponding to the strength receiving period (TI). However, sometimes, the transmitting signal and the strength detection timing are not synchronous, for example, just after reception of the transmitting signal from the capsule endoscope 203 by the receiving apparatus 202 is started. In that case, the receiving apparatus 202 executes antenna switching processing different from the above-described normal switching processing so as to search for a synchronization signal to restore synchronism.

Figure 20:
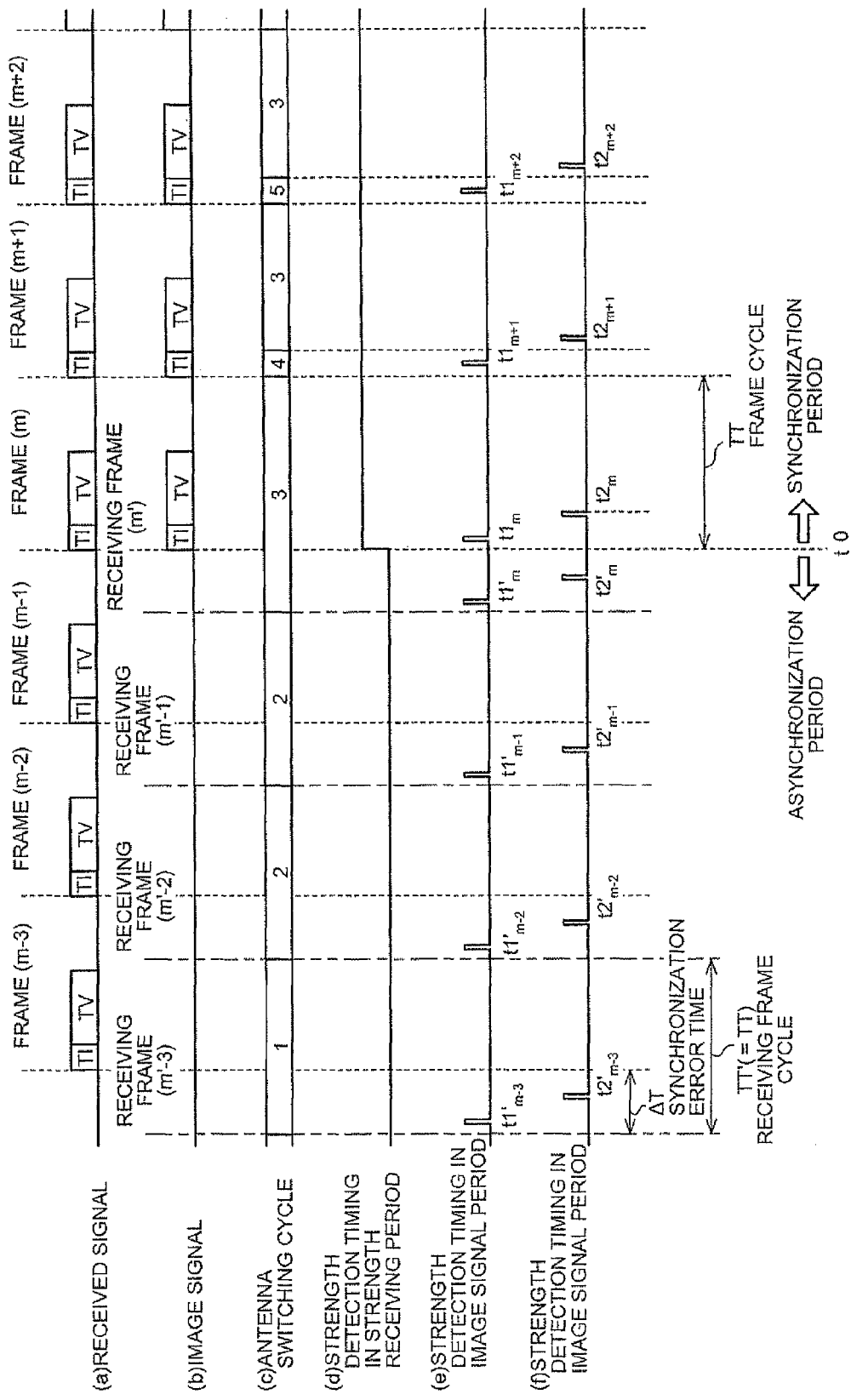
FIG. 20 is a time chart showing synchronous restoration antenna switching processing by the receiving apparatus shown in FIG. 16.

Here, the selection switching processing of the antennas 206a to 206h in case where the strength detection timing is not synchronous with the transmitting signal will be described with reference to FIG. 20. FIG. 20 is a time chart showing the antenna switching processing by the receiving apparatus 202, indicating asynchronous period in which the transmitting/receiving timing are not synchronous before time t0 when the frame (m) is started, and further indicating synchronous period in which the synchronism of the transmitting/receiving timing has been restored after time t0.

As shown in FIG. 20, in the asynchronous period, deviation in time is generated by synchronization error time ΔT between a frame (m−3) to (m−1) of the transmitting signal from the capsule endoscope 2 and a receiving frame (m'−3) to (m') indicating the receiving timing of the receiving apparatus 202 for convenience, so that neither timing $t1'_{m-3}$ to $t1'_m$ which is a strength detection timing in the strength receiving period nor timing $t2'_{m-3}$ to $t2'_m$ which is the strength detection timing of the image signal period is synchronous with the transmitting signal. Thus, the transmitting signal is not received by the image receiving antenna or the strength receiving antenna, so that the selection controller C1 cannot measure the receiving electric field strength based on the received strength signal S202. Further which of the antennas 206a to 206h can receive the transmitting signal cannot be determined. In the asynchronous period, each strength detection timing is generated by a predetermined receiving frame cycle TT' (=TT) based on the internal clock of the receiving apparatus 202.

To restore synchronism from such an asynchronous state, first, the selection controller C1 sets "0" in the synchronization signal detection/undetection variable N203 possessed by the switching controller SC if any synchronization signal is not received by the image receiving antenna or the strength receiving antenna at a current frame. The same antenna number is set in the strength-receiving-antenna number N201 and the image-receiving-antenna number N202 of a next frame. As the same antenna number, the selection controller C1 sets an antenna number different from the image receiving antenna and the strength receiving antenna of the current frame and then sets an antenna number next to the image receiving antenna of the current frame.

Next, the switching controller SC controls the sample holding circuit 215, A/D converter 216 and the selection controller C1 so as not to detect any received strength signal S202 in any of the strength receiving period and the image signal period of a next frame if the synchronization signal detection/undetection variable N203 is referred to and is "0". In this case, the switching controller SC controls the changeover switch SW so as to connect the antennas 206a to 206h corresponding to the same antenna numbers set by the selection controller C1 selectively over the entire period between the strength receiving period and the image signal period of the next frame.

Subsequent to the next frame, the selection controller C1 switches the antenna successively with the strength-receiving-antenna number N201 and the image-receiving-antenna number N202 kept as the same antenna number every predetermined number of frame periods, for example, every two frame periods, if any synchronization signal is not detected from the image signal S201 received by the antenna connected selectively as described above, so as to repeat reception of the transmitting signal to detect the synchronization signal. More specifically, as shown in FIG. 20, if no transmitting signal is detected with the antenna number No. 2 in two frame periods of receiving frame (m'−2) and (m'−1), the selection controller C1 changes the antenna number for receiving a next receiving frame (m') to No. 3 and repeats reception of the transmitting signal to detect the synchronization signal.

When any synchronization signal is detected by receiving the transmitting signal, the selection controller C1 sets "1" in the synchronization signal detection/undetection variable N203 and the switching controller SC corrects the strength detection timing of the strength receiving period and the image signal period based on the detected synchronization signal and restores synchronism of the receiving frame with respect to the frame of the transmitting signal. More specifically, as shown in FIG. 20, the switching controller SC corrects timings $t1'_m$, $t2'_m$ in the receiving frame (m') to timing $t1_m$, $t2_m$ based on the synchronization signal of the frame (m) detected by the antenna number No. 3 at time t0 so as to restore the synchronism of the receiving frame at the frame (m).

After the synchronism is restored, the selection controller C1 sets an antenna number next to the antenna which detects synchronism in the strength-receiving-antenna number N201 of a frame next to the restored frame and the antenna number of the antenna which detects synchronism is set continuously in the image-receiving-antenna number N202. For example, FIG. 20 shows a case where the antenna number No. 4 is set as the strength receiving antenna corresponding to the strength receiving period (TI) while the antenna number No.

3 is set continuously as an image receiving antenna corresponding to the image signal period (TV) in the next frame (m+1) in which synchronism is restored.

After that, the selection controller C1 and the switching controller SC execute normal antenna switching processing shown in FIG. 19 repeatedly. The selection controller C1 detects a synchronization signal from the image signal S201 at the head of each frame, sets "0" or "1" in the synchronization signal detection/undetection variable N203 based on a detection result and the switching controller SC executes the normal antenna switching shown in FIG. 19 if the synchronization signal detection/undetection variable N203 is "1" when it is referred to.

Figure 21:
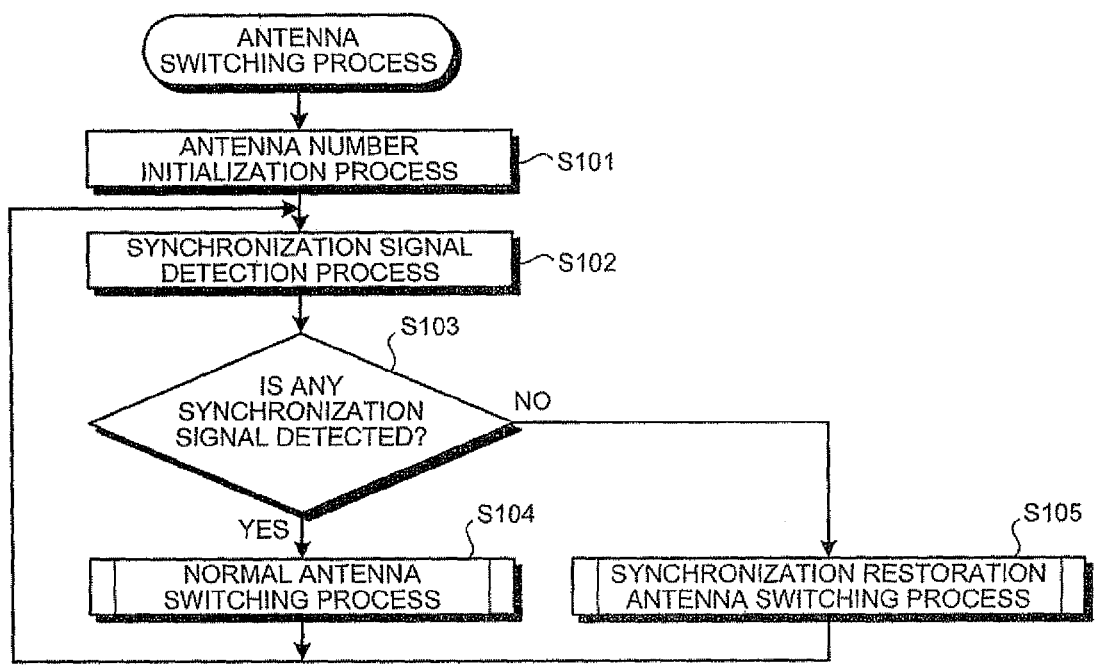
FIG. 21 is a flow chart showing antenna switching processing procedure by the receiving apparatus shown in FIG. 16.

Here, the procedure of the antenna switching processing which the receiving apparatus 202 carries out will be described with reference to the flow chart shown in FIG. 21. This antenna switching processing is carried out by the selection controller C1 and the switching controller SC. As shown in FIG. 21, as initial setting, the selection controller C1 executes antenna number initialization processing for initializing the strength-receiving-antenna number N201 and the image-receiving-antenna number N202 (step S101). In this step S101, the selection controller C1 sets antenna number No. 1 in image-receiving-antenna number N201 and sets antenna number No. 2 in strength-receiving-antenna number N201. In the meantime, the antenna numbers No. 1 to No. 8 which can be set here correspond to the antennas 206a to 206h as shown in FIG. 17.

Subsequently, the selection controller C1 detects a synchronization signal from the transmitting signal at the head of a frame and carries out synchronization signal detection processing for setting "0" or "1" in the synchronization signal detection/undetection variable N203 based on a detection result (step S102). Then, whether or not any synchronization signal is detected, that is, whether or not "1" is set in the synchronism detection/undetection variable N203 is determined (step S103) and if the synchronization signal is detected (step S103: Yes), the normal antenna switching processing in the synchronous period shown in FIG. 19 is carried out (step S104) and if any synchronization signal is not detected (step S103: No), the synchronism restoration antenna switching processing for restoration of synchronism in the asynchronous period shown in FIG. 20 is carried out (step S105). After that, the selection controller C1 and the switching controller SC execute the processing subsequent to step S102 repeatedly until a predetermined processing termination is instructed.

Figure 22:
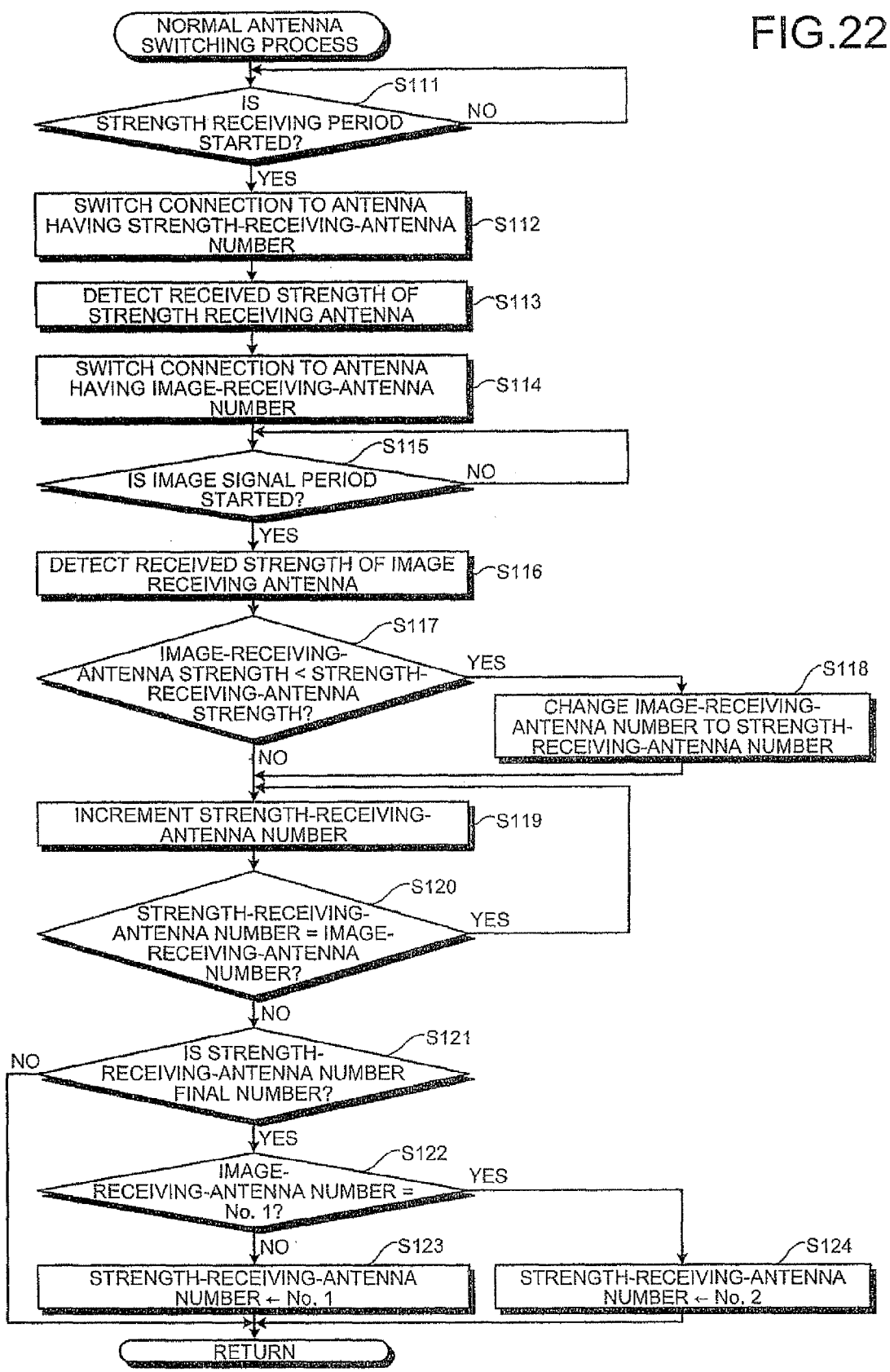
FIG. 22 is a flow chart showing normal antenna switching processing procedure shown in FIG. 21.

Next, normal antenna switching processing procedure in step S104 will be described with reference to the flow chart shown in FIG. 22. As shown in FIG. 22, the switching controller SC determines whether or not the strength receiving period is started (step S111). If the strength receiving period is started (step S111: Yes), the switching controller SC outputs an instruction for switching to an antenna corresponding to an antenna number set in the strength-receiving-antenna number N201 to the changeover switch SW (step S112) and the changeover switch SW switches to the instructed antenna. After that, the switching controller SC makes the sample hold circuit 215 and an A/D converter 216 execute the detection processing for the receiving electric field strength of the strength receiving antenna at the timing t1$_n$ shown in FIG. 19 (step S113).

Subsequently, the switching controller SC outputs an instruction for switching to an antenna set in the image-receiving-antenna number N202 in correspondence with a start of the image signal period to the changeover switch (step S114) and the changeover switch SW switches to an instructed receiving antenna. In the meantime, the switching period of this step S114 may not be a start of the image signal period and may be within the strength receiving period if the electric field strength measurement processing of the strength receiving antenna is terminated.

After that, the switching controller SC determines whether or not the image signal period has been started (step S115). The image signal period mentioned here may be a period in which the image signal is transmitted if any control signal is included in the image signal period. Then, if the image signal period is started (step S115: Yes), the sample holding circuit 215 and the A/D converting circuit 216 are made to detect the receiving electric field strength of the strength receiving antenna at timing t2$_n$, shown in FIG. 19.

Subsequently, the selection controller C1 determines whether or not the receiving electric field strength (image receiving antenna strength) of the image receiving antenna which is received in the image signal period is smaller than the receiving electric field strength (strength receiving antenna strength) of the strength receiving antenna which is received in the strength receiving period (step S117). If the image receiving antenna strength is smaller than the strength receiving antenna strength (step S117: Yes), the image-receiving-antenna number is set in the strength-receiving-antenna number N201 as a strength-receiving-antenna number (step S118) and the procedure proceeds to step S119. On the other hand, if the image receiving antenna strength is not smaller than the strength receiving antenna strength (step S117: No), or the image receiving antenna strength exceeds the strength receiving antenna strength, the value of the strength-receiving-antenna number N201 is incremented (step S119).

After that, whether or not the value of the strength-receiving-antenna number coincides with the value of the image-receiving-antenna number is determined (step S120) and in case of coincidence (step S120: Yes), the procedure proceeds to step S119, in which the value of the strength-receiving-antenna number is incremented and if not (step S120: No), whether or not the strength-receiving-antenna number is a final number (No. 8) is determined (step S121). If the strength-receiving-antenna number is not the final number (step S121: No), the procedure is returned to step S104 and if the strength-receiving-antenna number is the final number (step S121: Yes), whether or not the image-receiving-antenna number is No. 1 is determined (step S122).

Then, if the image-receiving-antenna number is not No. 1 (step S122: No), the selection controller C1 sets an antenna number No. 1 in the strength-receiving-antenna number N201 (step S123) and if the image-receiving-antenna number is No. 1 (step S122: Yes), antenna number No. 2 is set in the strength-receiving-antenna number N201 (step S124) and the procedure is returned to step S104.

Figure 23:
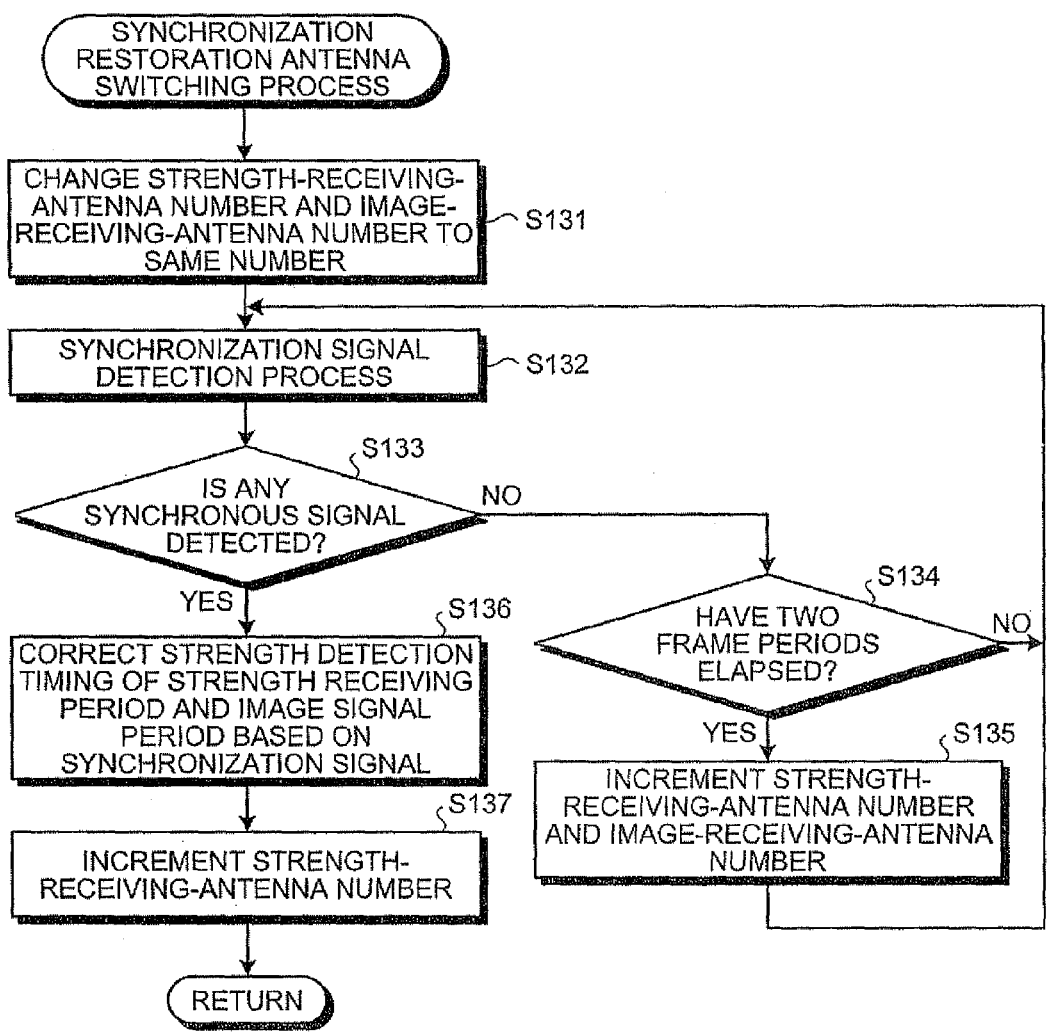
FIG. 23 is a flow chart showing the synchronous restoration antenna switching processing procedure shown in FIG. 21.

Next, synchronism restoration antenna switching processing procedure in step S105 will be described with reference to the flow chart shown in FIG. 23. As shown in FIG. 23, first, the selection controller C1 sets the strength-receiving-antenna number N201 and the image-receiving-antenna number N202 to the same antenna number (step S131). Subsequently, the selection controller C1 detects a synchronization signal from the transmitting signal in a predetermined frame period, for example, in a period of two frames and carries out synchronization signal detection processing of setting "0" or "1" in the synchronization signal detection/undetection variable N203 based on a result of the detection (step S132) so as to determine whether or not any synchronization signal is detected, or whether or not "1" is set in the synchronism detection/undetection variable N203 (step S133).

If any synchronization signal is not detected (step S133: No), the selection controller C1 determines whether or not a predetermined frame cycle, for example, two frame cycles have elapsed (step S134) and if the two frame cycles have not elapsed (step S134: No), the processing after step S132 is repeated. Further, if two frame cycles have elapsed (step S134: Yes), the strength-receiving-antenna number N201 and image-receiving-antenna number N202 are incremented (step S135) and after that, processing after step S132 is repeated.

On the other hand if any synchronization signal is detected (step S133: Yes), the switching controller SC corrects the strength detection timing of the strength receiving period and image signal period based on the detected synchronization signal so as to restore the synchronism of transmitting/receiving (step S136). After that, the selection controller C1 increments the strength-receiving-antenna number N201 (step S137) and the procedure is returned to step S105. In the meantime, an antenna number at the time of synchronism restoration is set in the image-receiving-antenna number N202 continuously.

As described above, the receiving apparatus 202 of the fifth embodiment measures the receiving electric field strength of image signal in the image signal period, and then switches to other receiving antenna than the receiving antenna which receives image signal in the strength receiving period so as to measure the receiving electric field strength. If the receiving electric field strength measured in the strength receiving period exceeds a receiving electric field strength measured in the image signal period, the receiving antenna switched in this strength receiving period is switched to the receiving antenna in the image signal period. Consequently, the strength receiving period can be shortened and a time taken for switching of the receiving antenna in the strength receiving period can be provided with an allowance. As a result, the configuration for the switching of the antenna and measurement of the receiving electric field strength are not demanded to have high speed performance, thereby the configuration being simplified.

The synchronization signal detection/undetection variable N203 is referred to and if any synchronization signal in the transmitting signal is detected, the normal antenna switching processing is carried out and if any synchronization signal is not detected, antenna switching processing for restoring synchronism is carried out. Consequently, the receiving electric field strength can be measured securely and the image signal can be received securely through an antenna selected based on this measurement result, thereby improving certainty and reliability of receiving operation further.

Next, a sixth embodiment of the present invention will be described. The sixth embodiment includes a peak hold circuit 218 between the receiving circuit 211 and the sample holding circuit 215 of the fifth embodiment.

Figure 24:
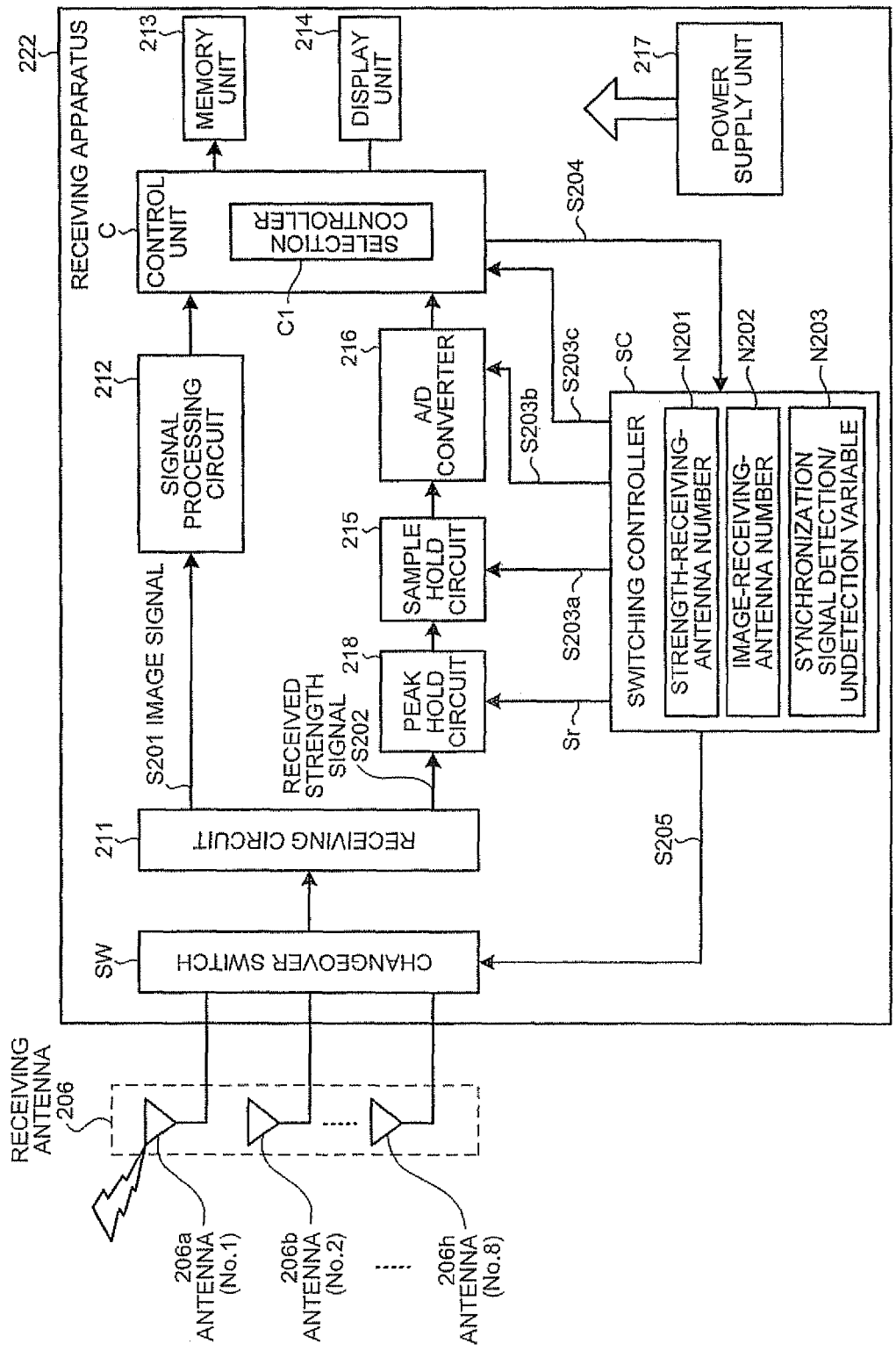
FIG. 24 is a block diagram showing the configuration of the receiving apparatus according to a sixth embodiment of the present invention.

FIG. 24 is a block diagram showing the configuration of the receiving apparatus 222 of the sixth embodiment. As shown in FIG. 24, the receiving apparatus 222 further includes the peak hold circuit 218 in the configuration of the receiving apparatus 202 so as to hold a peak value of received strength signal S202 output from the receiving circuit 211.

Thus, the switching controller SC outputs a signal Sr to the peak hold circuit 218 at the start of the strength receiving period so as to reset the peak hold at timing tr1 as shown in FIG. 25. After that, the switching controller SC acquires a peak value held by the peak hold circuit 218 at a detection timing t3 of the sample holding circuit 215 so as to reset the peak holding circuit 218 again at a timing tr2 at a start of the image signal period. At a timing t4 after this timing tr2, the sample holding circuit 215 acquires a peak value held by the peak holding circuit 218. In other words, the sample holding circuit 215 can sample a peak value between timing tr1 and timing t3 and a peak value between timing tr2 and timing t4, thereby receiving electric field strength being measured at a high accuracy.

When a synchronization signal is detected in the synchronism restoration antenna processing, the switching controller SC corrects the peak hold reset timing as well as the strength detection timing of the strength receiving period and image signal period based on a detected synchronization signal as shown in FIG. 26 and restores synchronism of the receiving frame with respect to the frame of a transmitting signal. That is, timings $t3'_{m'}$, $t4'_{m'}$ in the receiving frame (m') are corrected to timings $t1_m$, $t2_m$ based on the synchronization signal of the frame (m) detected by the antenna number No. 3 at time t0 and reset timings $tr1'_m$, $tr2'_m$ are corrected to timings $tr1_m$, $tr2_m$ and then, the synchronism of the receiving frame is restored at the frame (m).

According to the Embodiments 5 and 6, the antenna switching processing is carried out with a simple configuration without any high speed processing by switching the antennas successively at every frame cycle. Alternatively, it is permissible to realize the antenna switching processing capable of switching all the antennas within a frame cycle using a circuit configuration which enables high speed switching and execute the synchronism restoration antenna switching processing in a single frame cycle in the asynchronous period so as to restore the synchronism quickly.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus for receiving radio signals including image information transmitted by a mobile transmitting device through a plurality of receiving antennas, comprising:
    a plurality of frequency converters for outputting modulated signals obtained by converting respective radio signal received through the plurality of receiving antennas by different modulation frequencies;
    a superposing unit for superposing each of the modulated signals generated by the plurality of frequency converters on a frequency axis;
    a cable with a single coaxial cable where each of the modulated signals superposed by the superposing unit is transmitted; and
    a receiving unit for demodulating each modulated signal input through the cable to receive and output the image information;
    wherein the receiving unit includes:
    a plurality of demodulating units for demodulating the respective modulated signals output from the superposing unit to output base band signals thereof; and
    a signal processing unit for generating a base band signal having a high likelihood based on the plurality of the base band signals output from the demodulating units, and generating and outputting image information based on the base band signal.

2. The receiving apparatus according to claim 1, wherein the signal processing unit synthesizes and outputs the plurality of the base band signals.

3. The receiving apparatus according to claim 1, wherein the signal processing unit selects and outputs received image information having fewest errors.

4. The receiving apparatus according to claim 1, wherein the receiving unit includes
- wherein the plurality of demodulating units further output signal strength signals each indicating a signal strength;
- a switching unit for switching outputs of the demodulating units;
- a selection instruction unit for selecting one of the demodulating units which demodulates a modulated signal having a highest signal strength based on the signal strength signals output from the demodulating units to output a switching instruction signal to the switching unit; and
- the signal processing unit generating and outputting the image information based on the base band signal output from the demodulating unit selected by the switching unit.

5. The receiving apparatus according to claim 1, further comprising a flexible flat cable connecting between the plurality of antennas and the superposing unit, wherein the frequency converters are planar circuits formed on the flat cable.

* * * * *